United States Patent
Gifford, III et al.

(10) Patent No.: US 6,905,503 B2
(45) Date of Patent: Jun. 14, 2005

(54) METHODS AND DEVICES FOR DELIVERING OCCLUSION ELEMENTS

(75) Inventors: Hanson S. Gifford, III, Woodside, CA (US); Ivan Sepetka, Los Altos, CA (US); Son Gia, San Jose, CA (US); Maria Aboytes, East Palo Alto, CA (US); Ryan Pierce, Mountain View, CA (US); Tina Patel, San Carlos, CA (US); Christopher Ken, San Mateo, CA (US)

(73) Assignee: Concentric Medical, Inc., Mountain View, CA (US)

( * ) Notice: Subject to any disclaimer, the term of this patent is extended or adjusted under 35 U.S.C. 154(b) by 414 days.

(21) Appl. No.: 10/072,825

(22) Filed: Feb. 8, 2002

(65) Prior Publication Data

US 2002/0133189 A1 Sep. 19, 2002

Related U.S. Application Data

(63) Continuation-in-part of application No. 09/780,587, filed on Feb. 9, 2001, now Pat. No. 6,494,884.

(51) Int. Cl.[7] .............................................. A61B 17/00
(52) U.S. Cl. ...................................... 606/108; 606/151
(58) Field of Search ................................. 606/108, 151, 606/157, 114, 127, 113, 200

(56) References Cited

U.S. PATENT DOCUMENTS 5,522,836 A * 6/1996 Palermo ...................... 606/108
5,984,929 A * 11/1999 Bashiri et al. ............... 606/108

* cited by examiner

Primary Examiner—Kevin T. Truong
(74) Attorney, Agent, or Firm—Jens E. Hoekendijk

(57) ABSTRACT

A device for delivering an occlusion element, or other medical device, which includes a fluid dissolvable bond. The occlusion element is coupled to the delivery element with the fluid dissolvable bond. The bond may be dissolved by delivering a fluid through the delivery element either through the delivery element itself or through a tube positioned in the delivery element.

65 Claims, 23 Drawing Sheets

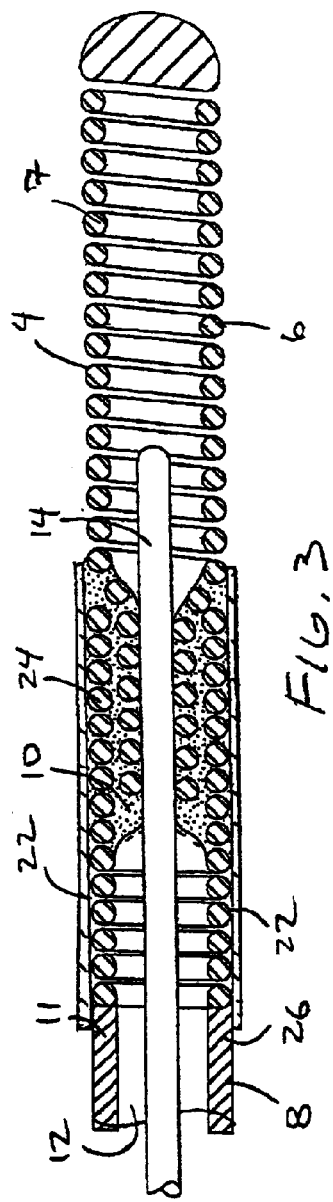
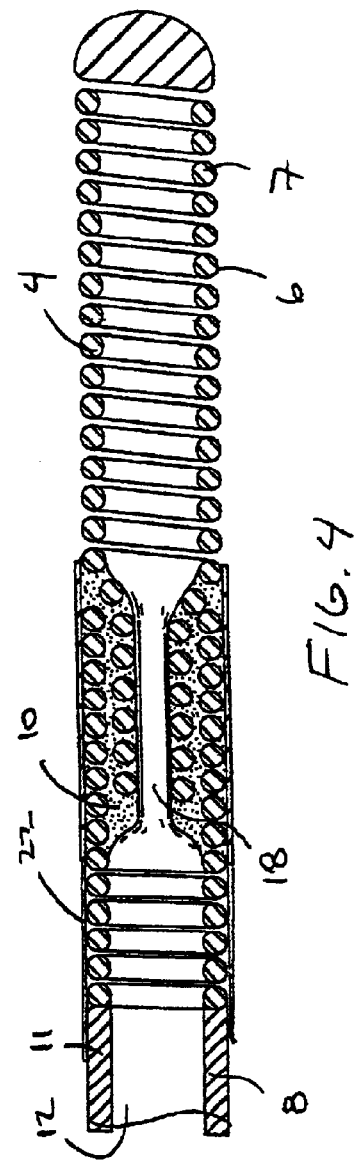
FIG. 3
FIG. 4

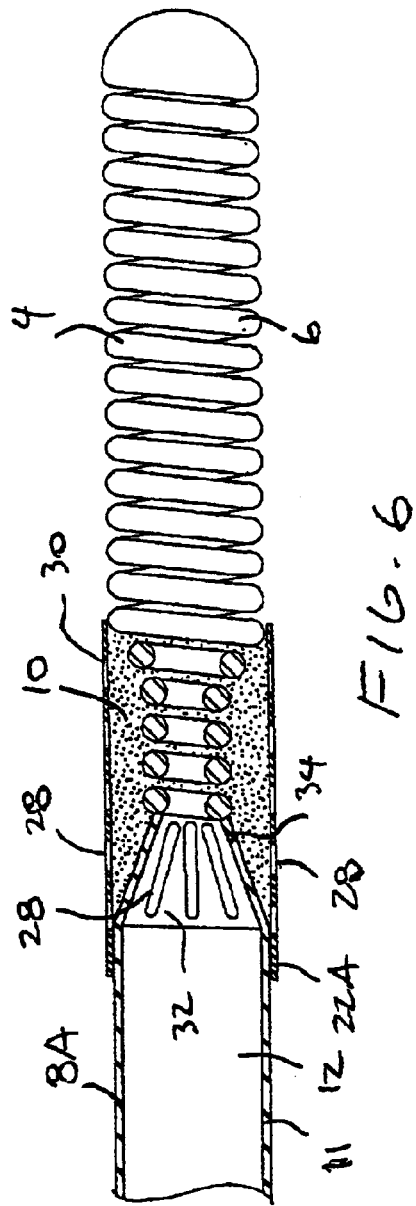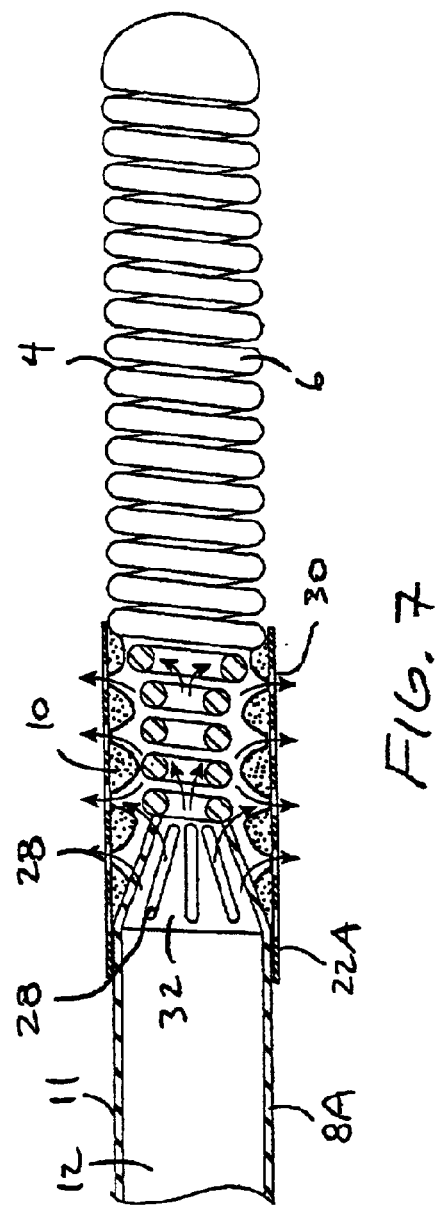

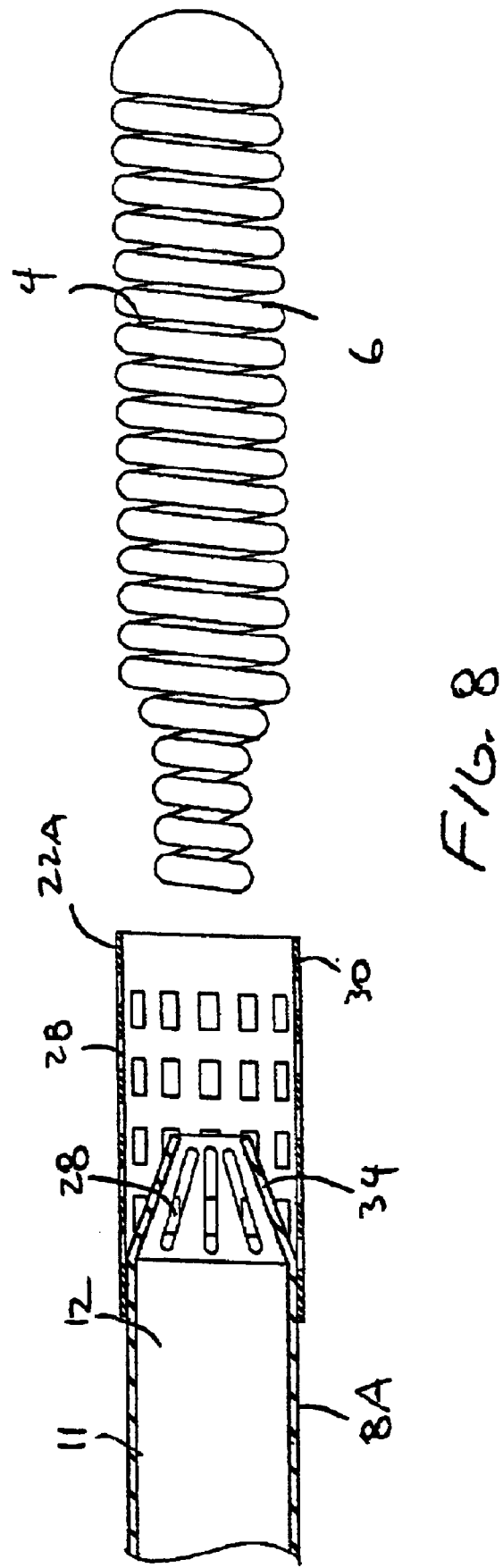

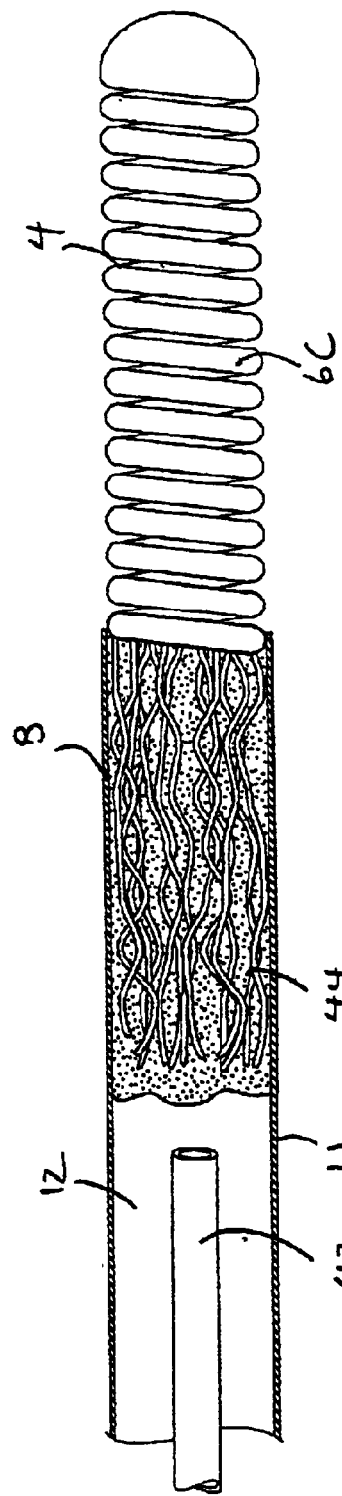
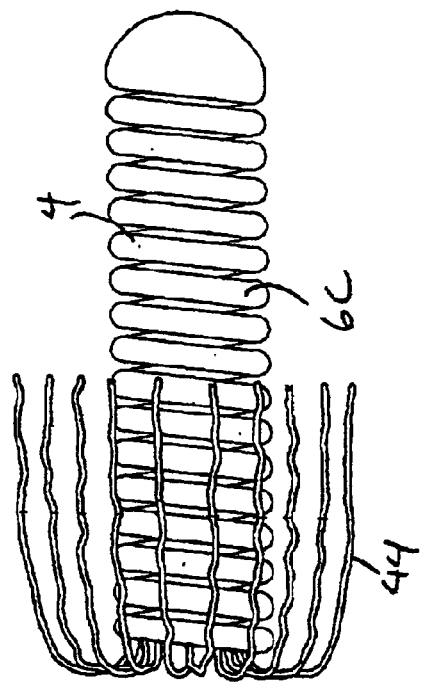
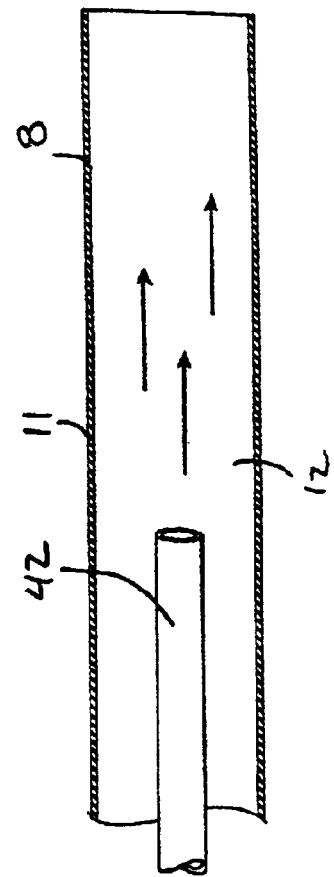
FIG 11
FIG 12

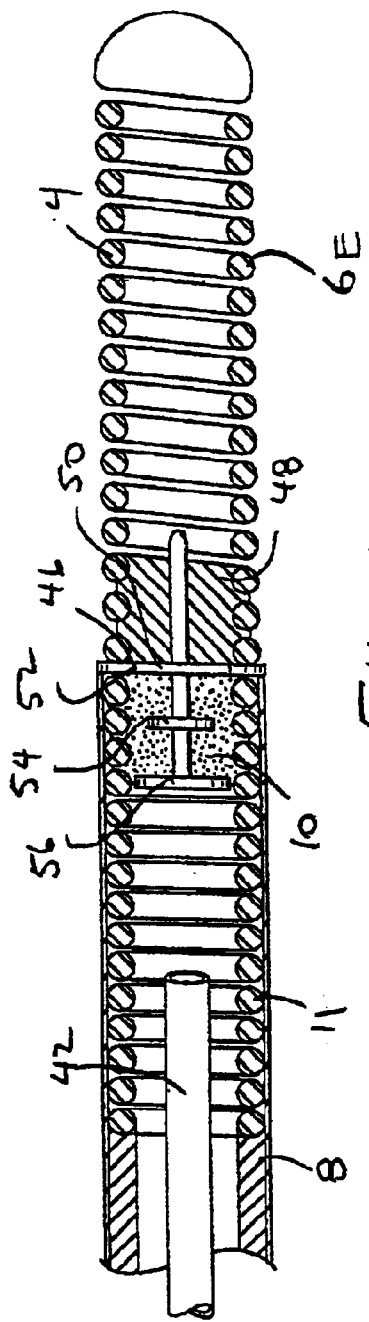
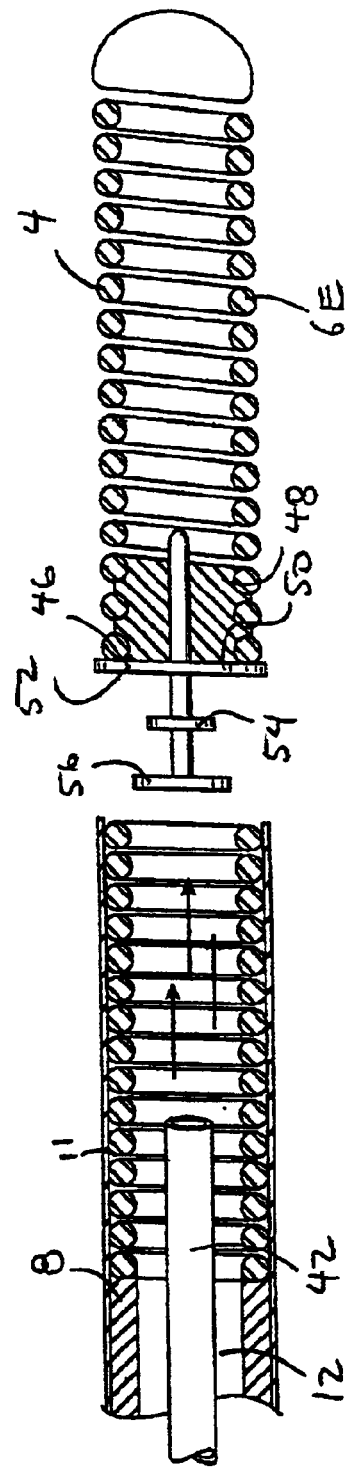

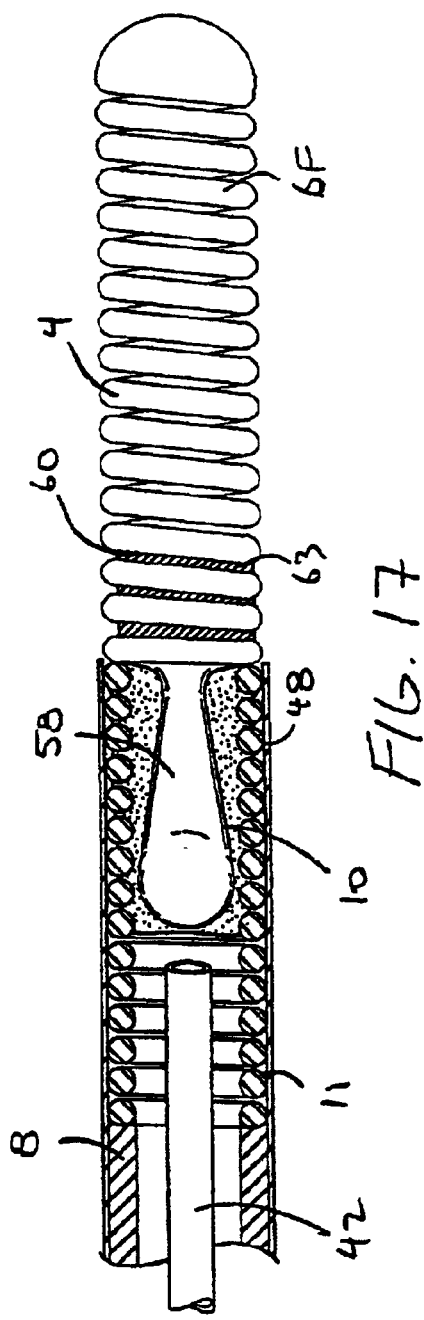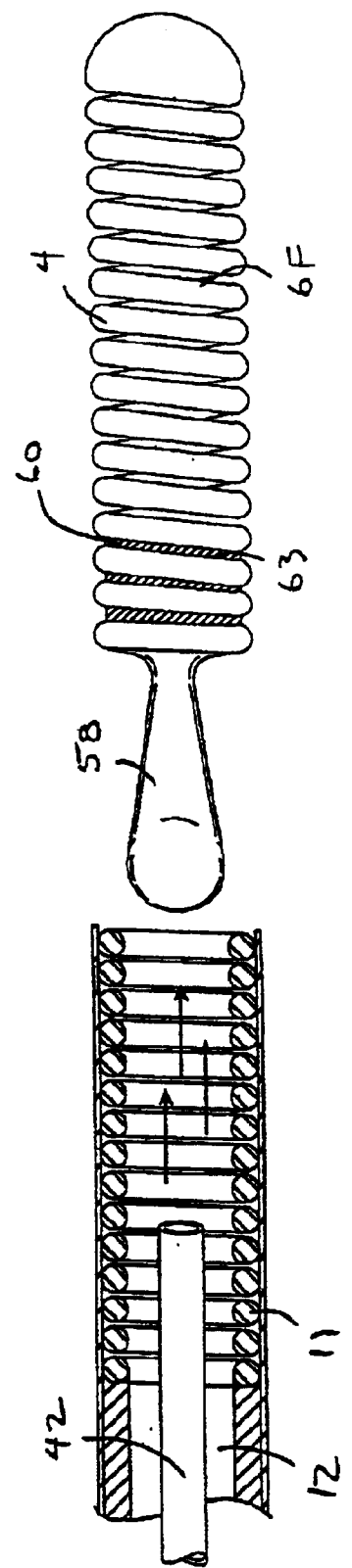

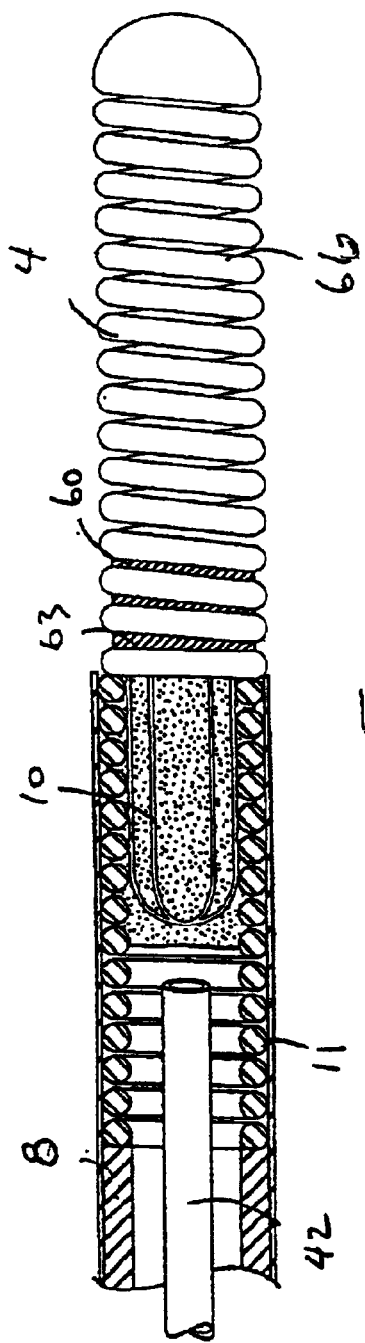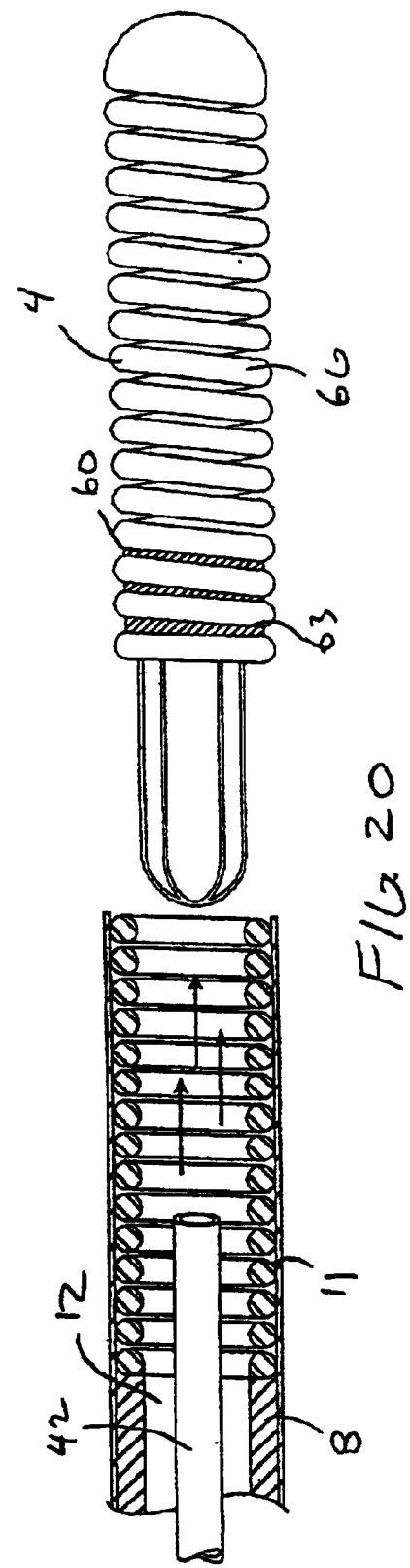

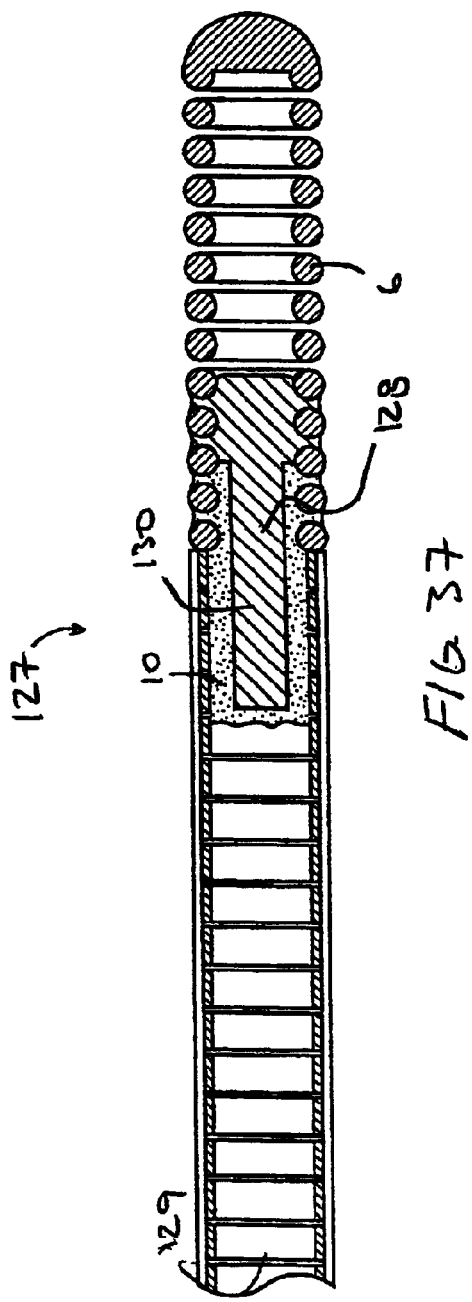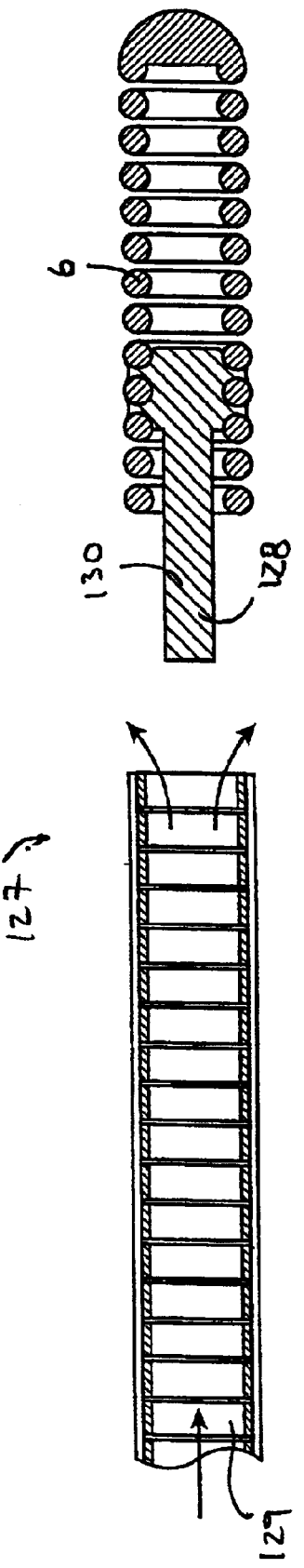
FIG. 37
FIG. 38

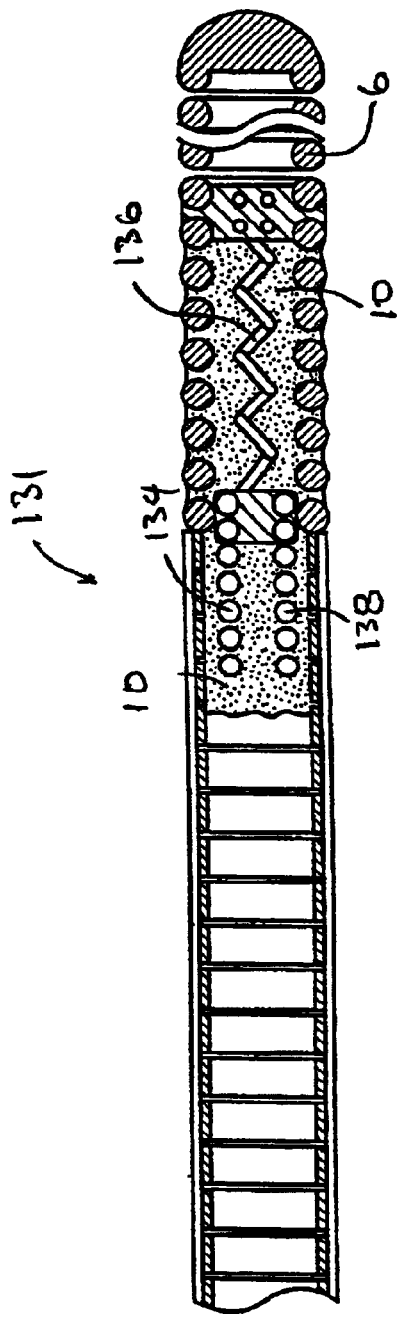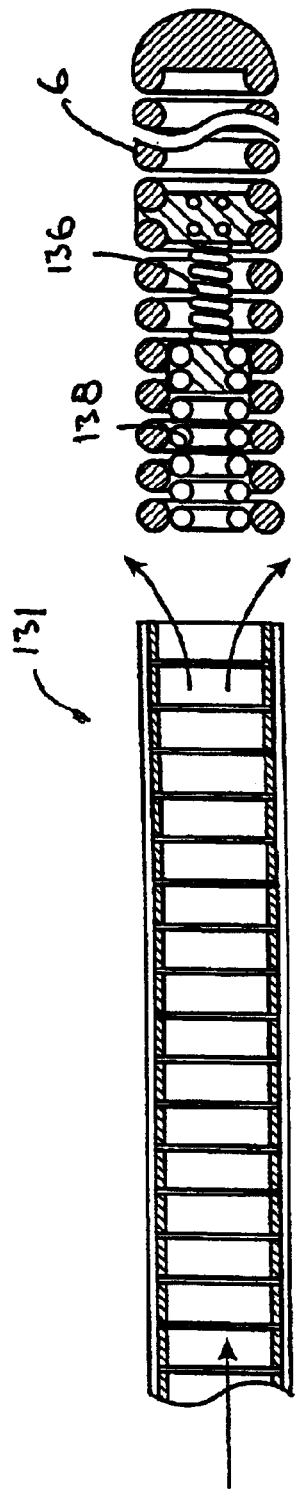

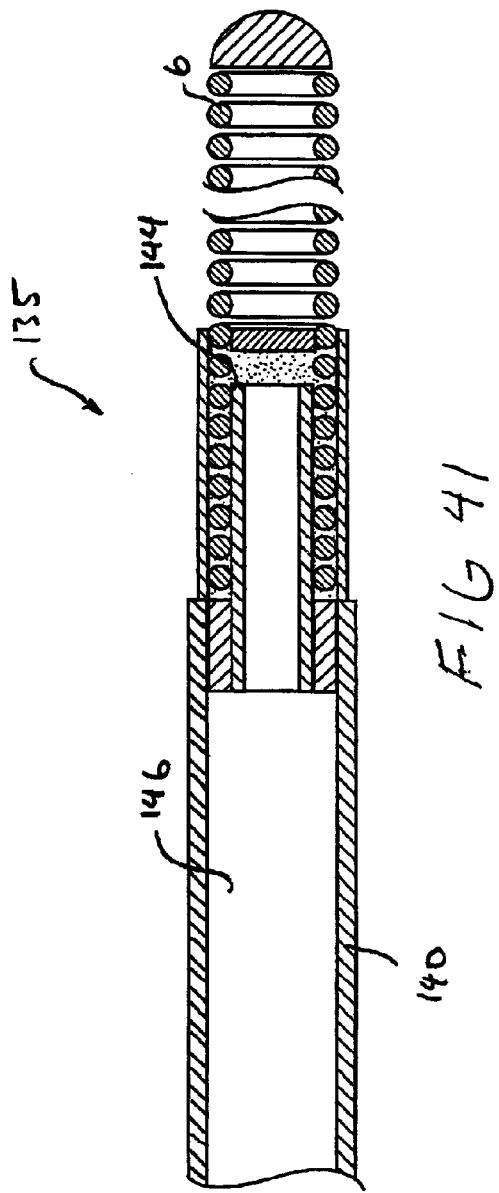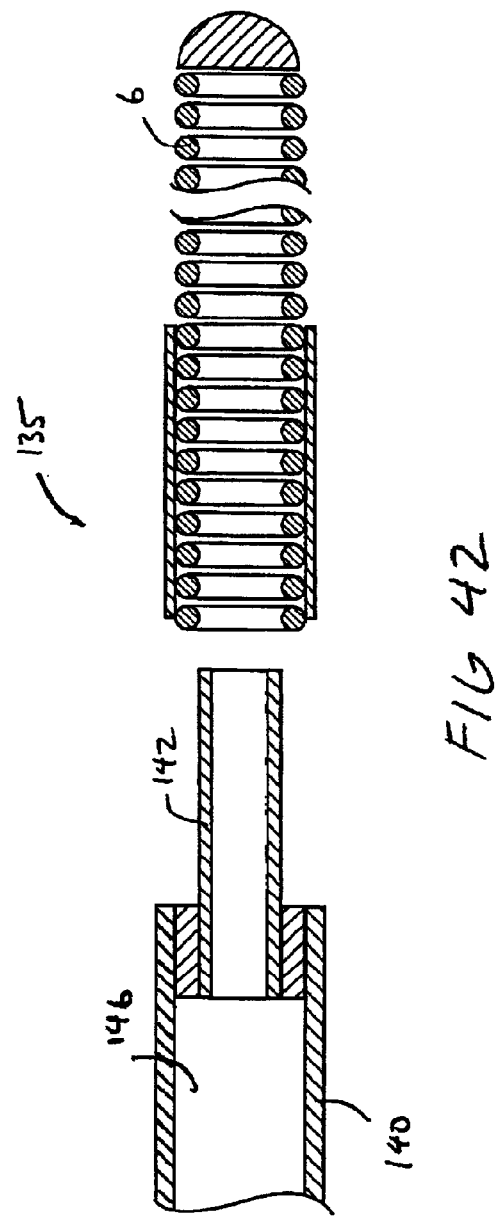

METHODS AND DEVICES FOR DELIVERING OCCLUSION ELEMENTS

CROSS REFERENCE TO RELATED APPLICATIONS

The present application is a continuation-in-part of Methods and Devices for Delivering Occlusion Elements, Ser. No. 09/780,587, filed Feb. 9, 2001 now U.S. Pat. No. 6,494,884, the full disclosures of which are incorporated herein by reference.

BACKGROUND OF THE INVENTION

The present invention relates to the delivery of medical devices and, in particular, occlusion elements. Occlusion elements, such as coils, are delivered to occlude vascular regions and malformations for various reasons. For example, occlusion elements, such as coils, may be delivered into an aneurysm to occlude the aneurysm. Other uses of occlusion elements include treatment of AVM's and other malformations.

SUMMARY OF THE INVENTION

The medical device, such as the occlusion element, is coupled to a delivery element with a material which is dissolvable with a fluid. The material forms a dissolvable connection between the delivery element and the occlusion element. The occlusion element is advanced through the patient's vascular system and, at the appropriate time, the material is dissolved. The dissolvable material is preferably dissolved with a fluid which is delivered to the material through the delivery element or through a tube positioned in the delivery element. The fluid may be delivered, withdrawn or otherwise circulated around the material with the tube and delivery element in any suitable manner. Alternatively, the material may be dissolved with the patient's own blood. Finally, the fluid may also be contained within the delivery element but separated from the material until the desired time. Although the present invention provides a few exemplary fluids and dissolvable materials, the fluid and dissolvable material combination may be any suitable combination without departing from the scope of the invention.

The occlusion element may be embedded in the material. For example, the occlusion element may have a coil, a plurality of filaments, a ball or a cage embedded in the material. The embedded portion may also be in a biased position, either expanded or collapsed, when embedded in the material. In this manner, the embedded portion helps to mechanically disturb the dissolvable portion to release the device as the material dissolves. For example, the embedded portion may be a stacked coil which expands when released. The delivery element itself may also have a portion embedded in the material, such as a number of filaments, to further secure the delivery device to the occlusion element.

A blocking element may also be provided which protects part of the dissolvable material from exposure to blood or other fluids. The blocking element may be positioned within a cavity in the material. The cavity may be a throughhole through which the fluid is delivered when dissolving the material. The blocking element may also help to protect the connection from kinking and other mechanical disturbances which occur when advancing the occlusion element through small, tortuous vessels. The blocking element can prevent inadvertent mechanical detachment when the device is bent or otherwise deformed during advancement through the patient. The occlusion element itself may also have a blocking portion which prevents contact between the patient's blood and the material thereby inhibiting premature dissolution of the material. The blocking portion may be a plug of material such as solder.

A flexible sheath may also be positioned over the material to protect the material. The sheath may be solid or may have openings or slits therein to promote flow through the sheath when dissolving the material. The delivery element may also have a fluid distributing portion which distributes the fluid for dissolution of the material.

These and other advantages of the invention will become apparent from the following description of the preferred embodiments, claims and drawings.

BRIEF DESCRIPTION OF THE DRAWINGS

FIG. 3 shows the occlusion element mounted to a delivery element.

FIG. 4 shows the distal end of the delivery element with a blocking element removed from a cavity in the dissolvable material.

FIG. 6 shows another device for delivering the occlusion element.

FIG. 7 shows the device of FIG. 6 after partial dissolution of the material.

FIG. 8 shows the occlusion element released from the delivery device.

FIG. 11 shows yet another device for delivering an occlusion element.

FIG. 12 shows the occlusion element of FIG. 11 released from the delivery element.

FIG. 15 shows another device for delivering an occlusion element with the occlusion element inhibiting fluid contact with the material.

FIG. 16 shows the occlusion element of FIG. 16 released from the delivery element.

FIG. 17 shows still another device for delivering an occluding element.

FIG. 18 shows the occlusion element of FIG. 17 released from the delivery element.

FIG. 19 shows still another device for delivering an occluding element.

FIG. 20 shows the occlusion element of FIG. 19 released from the delivery element.

FIG. 37 shows still another system for delivering a medical device, such as the occlusion element, with a threaded portion embedded in the dissolvable material.

FIG. 38 shows the material dissolved and the threaded portion released.

FIG. 39 shows another system for delivering an occlusion element which has preloaded portion embedded in the dissolvable material.

FIG. 40 shows the preloaded portion released.

FIG. 41 shows another system for delivering the occlusion element.

FIG. 42 shows the system of FIG. 41 with the occlusion element released.

DESCRIPTION OF THE PREFERRED EMBODIMENTS

Figure 1:
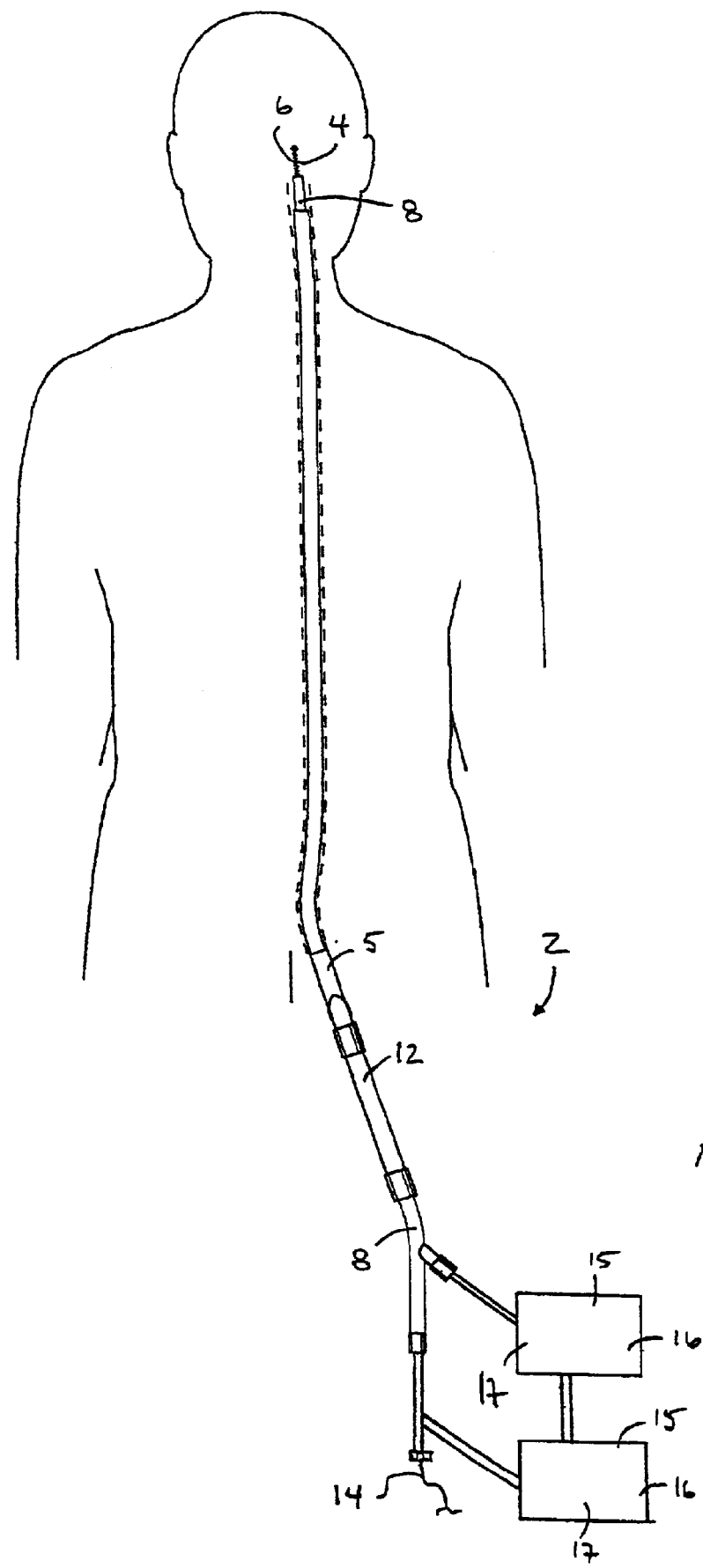
FIG. 1 shows a system of the present invention.
Figure 2:
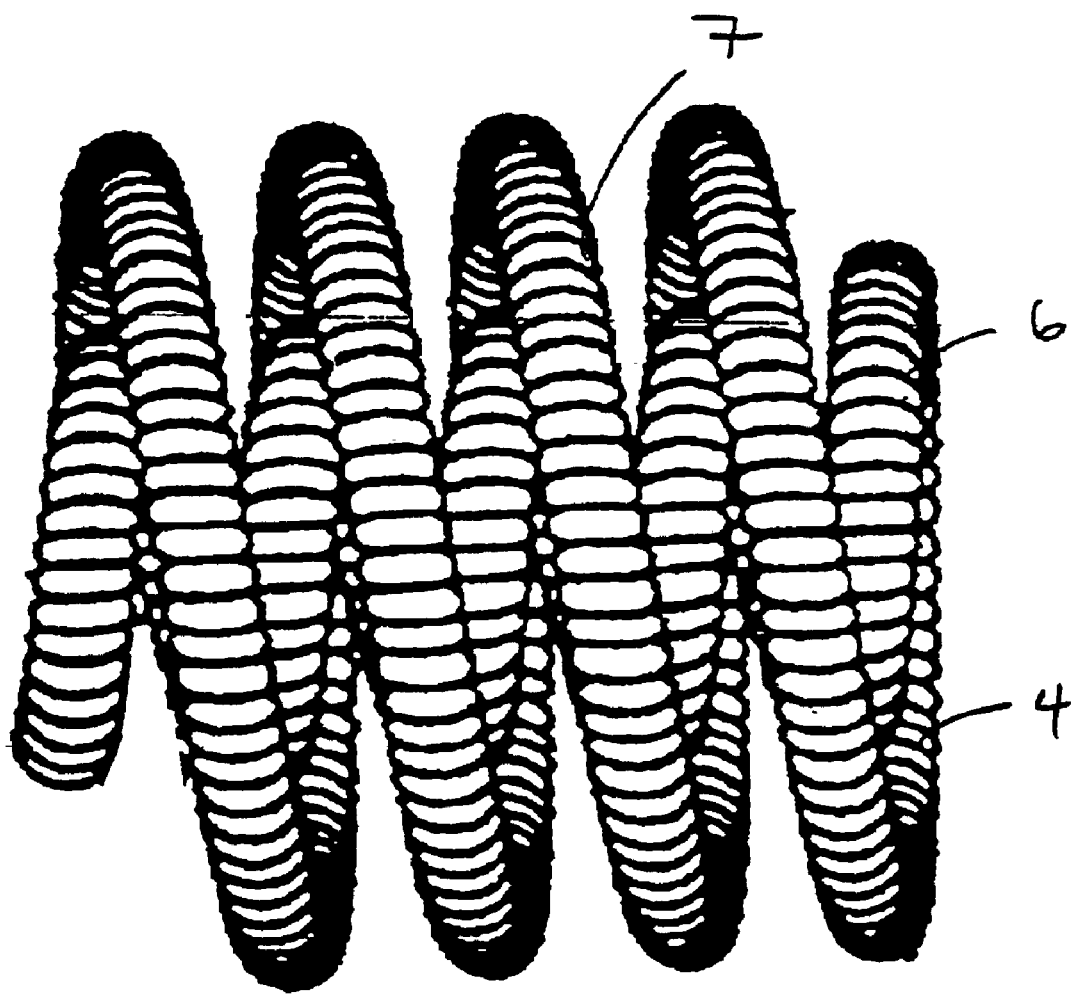
FIG. 2 shows an occlusion element.
Figure 5:
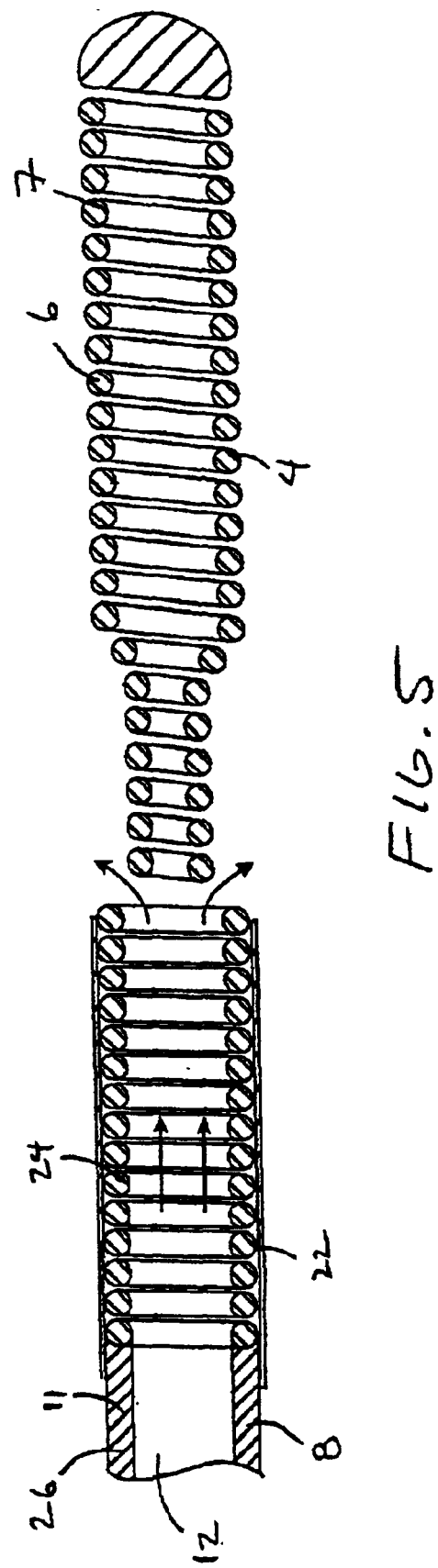
FIG. 5 shows the distal end of the delivery element with the dissolvable material dissolved and the occlusion element released.

Referring to FIGS. 1–4, a system 2 for delivering a medical device 4, such as an occlusion element 6, is shown. The invention is described in connection with delivery of the occlusion element 6, however, the devices and methods of the present invention may be used to deliver any other medical device to any part of the body without departing from the scope of the invention. The system 2 includes a delivery element 8 to which the occlusion element 6 is mounted. A fluid dissolvable material 10 forms a dissolvable connection between the occlusion element 6 and the delivery element 8. For example, the material may be a sugar (such as mannitol), salt or combination thereof or the material may be a polymer which is dissolved with a fluid having a specific pH range. These and other examples and combinations of fluid and dissolvable material 10 are provided below. The material 10 and fluid used to dissolve the material 10 may be any suitable combination and numerous combinations not described herein may be used without departing from the scope of the invention.

The occlusion element 6 is shown as a short section of coil for clarity but may be any suitable occlusion element 6 such as those described in U.S. Pat. Nos. 5,855,578, 5,853,418, 5,749,894 and 5,749,891 which are hereby incorporated by reference. In the preferred embodiment, the occlusion element 6 is made of platinum wire or ribbon which forms coils 7. Of course, any suitable materials and structure may be used to form the occlusion element 6. The delivery element 8 is preferably a tube 11 having at least one lumen 12, however, the delivery element 8 may also be a solid element such as a wire or mandrel without departing from the scope of the invention. The occlusion element 6 is mounted to the end of the delivery element 8 and extends from the delivery element.

The system 2 of FIG. 1 shows delivery of the occlusion element 6 to the cerebral vasculature, however, the system, devices and methods of the present invention may be used to deliver the occlusion element 6, or other medical device, to any location in the patient. The system 2 includes a guide catheter 5 which is advanced to a suitable location. A microcatheter or sheath 12 may then be advanced through the guide catheter 5. The delivery element 8 is then advanced through the microcatheter 12 to the desired release site. The microcatheter or sheath 12 may hold the occlusion element 6 in a collapsed condition as demonstrated in the patents incorporated by reference above. The element 6 forms the coiled structure of FIG. 2 as it exits the distal end of the sheath 12. The delivery element 8 may receive a blocking element 14 which is described in further detail below. A fluid circulating device 15, such as a source of fluid 16, is coupled to the delivery element 8 for delivery of the fluid that dissolves the material 10. The fluid may be any suitable fluid such as saline but may also be the patient's own blood, a mixture of saline and contrast to visualize the area or any combination thereof.

The occlusion element 6 is mounted to the delivery element 8 with the fluid dissolvable material 10 which forms a dissolvable bond or connection 11. The fluid is preferably delivered to the dissolvable material 10 from the source of fluid 16 so that the dissolution of the material 10 may be controlled by delivery of the fluid. Although it is preferred to deliver the fluid to dissolve the material 10, however, the fluid may also simply be the patient's own blood. Such a device may be practiced with various aspects of the invention described herein without departing from the scope of the invention.

The fluid may simply erode or dissolve the bond 12 or the material 10 may be dissolved with additional chemical, thermal or mechanical action. For example, the fluid may be an acid, base or other ionic fluid which chemically dissolves the material 10. For example, hydrogen chloride may be used to dissolve a connection having zinc or hydrogen peroxide may be used to dissolve a connection having iron. The fluid 16 and material 10 may also form a solvent/solute relationship such as Hypan dissolved by a fluid such as dimethyl sulfoxide.

In still another example, the material 10 may be a cross-linked polymer such as a cross-linked alginate. The alginate may dissolve in the presence of a suitable fluid containing a monovalent, divalent, or trivalent cation such as saline. The alginate may be cross-linked in any suitable manner such as with calcium chloride.

In still another example, the material may be a polymer which preferentially dissolves upon a pH or salinity change or upon application of an electric field. Such a polymer is sold under the trade name EUDRAGIT® by Rohm GmbH of Darmstadt, Germany, which is an acrylic polymer and more specifically a methacrylate polymer. The polymer compound has polymer layers bonded together with hydrogen bonds in alternating layers of positive and negative charge. The bond between the polymer layers is broken by application of the pH or salinity change or upon application of an electric field. For example, the fluid 16 may also have a pH which dissolves the material 10 faster than the pH of other fluids which the material 10 is exposed to. Thus, if the material 10 is exposed to blood, saline, contrast and the like, the dissolvable material 10 is preferably selected to at least dissolve slowly, if at all, at the pH of these fluids and more quickly when exposed to the appropriate pH fluid. In a preferred embodiment, the material dissolves at least three times faster, and more preferably at least five times faster at the selected pH than at the pH of other fluids to which it is exposed. The dissolution rate can also be enhanced by flowing fluid into contact with the dissolvable material.

Once the occlusion element is at the desired location, a fluid, such as sodium bicarbonate, having the appropriate pH is delivered to dissolve the material 10. As mentioned above, the material 10 may dissolve slowly in the fluids to which it is exposed so long as the material dissolves faster when exposed to the appropriate fluid. EUDRAGIT®, for example, dissolves slowly in blood or saline, however, the polymer dissolves much faster with the appropriate fluid. In a preferred embodiment, the fluid has a pH of either about 4–6 or about 8–9.5.

In a specific example, EUDRAGIT® L100 and S100 (1:1) are dissolved with an ethyl alcohol/water (95:5 by weight) solvent at a ratio of 0.05 G EUDRAGIT® per gram of solution using a magnetic mixer. Small drops of the EUDRAGIT® solution are then applied to the appropriate area between the medical device or element and the delivery or insertion element. The drop is then dried which may take 1–5 hours during which time the solvent substantially evaporates leaving the EUDRAGIT® material to form the dissolvable bond. If necessary or desired, additional drops or coatings may be applied after the previous drop, coating or application has dried.

Thus, it can be appreciated from the various examples provided above that a number of different combinations of fluid and dissolvable material may be used and numerous other combinations are possible without departing from the invention.

Referring again to FIG. 3, the blocking element 14 may be used to protect parts of the dissolvable material 10 during introduction and advancement of the occlusion element 6. The blocking element 14 may simply be a wire, guidewire, mandrel or even a tube. The blocking element 14 may be positioned adjacent or against any portion of the material 10 and is preferably positioned in a cavity 18 in the material 10. The cavity 18 is shown as a throughhole 20 but may take any other shape such as a hole closed on one end. The blocking element 14 temporarily blocks the cavity 18 to inhibit dissolution of the material 10. When the blocking element 14 is withdrawn, part of the material 10 is exposed thereby permitting dissolution of the material 10. Of course, fluid may be in contact with the material 10 even with the blocking element 14 positioned in the cavity, however, the blocking element 14 will at least inhibit fluid flow around the dissolvable material 10 thereby preventing premature dissolution of a substantial portion of the material 10.

The delivery element 8 may include a sheath 22 extending over an outer surface of the dissolvable material 10. The sheath 22 protects the outer surface of the material 10 to inhibit dissolution of the material 10. The sheath 22 may be any suitable flexible sheath and may be made of any suitable material such as PET. The delivery element 8 has a coil 24 coupled to a tube 26. The coil 24 provides a flexible distal end for advancement of the delivery element 8 through tortuous vessels. The sheath 22 may extend over the coil 24 and tube 26 or only over a portion of the coil 24 and material 10.

Referring to FIGS. 6–8, another device for delivering the occlusion element 6 is shown wherein the same or similar reference numbers refer to the same or similar structure. The delivery element 8A has openings 28 therein through which fluid is delivered when dissolving the material 10. The openings 28 may be in the sheath 22A extending over the material 10. The openings 28 may also be one or more slits 30 in the sheath 22A which open when positive pressure is applied so that the slit 30 acts as a valve which opens when the fluid is delivered yet covers the material 10 during introduction and advancement. The openings 28 may also be part of a portion 32 of the delivery element 8 that extends into the material 10. The portion 32 extending into the material 10 may, for example, be a conical section 34. The openings 28 serve as fluid channels when dissolving the material 10 so that the material 10 may be dissolved relatively quickly at the desired time. An advantage of such a design is that the dissolvable material 10 may be kept relatively robust while maintaining the ability to quickly dissolve the bond at the appropriate time. Use of the blocking element 14 (FIG. 2) further enhances the ability to control dissolution of the dissolvable material 10 as discussed above and specifically incorporated here.

Figure 9:
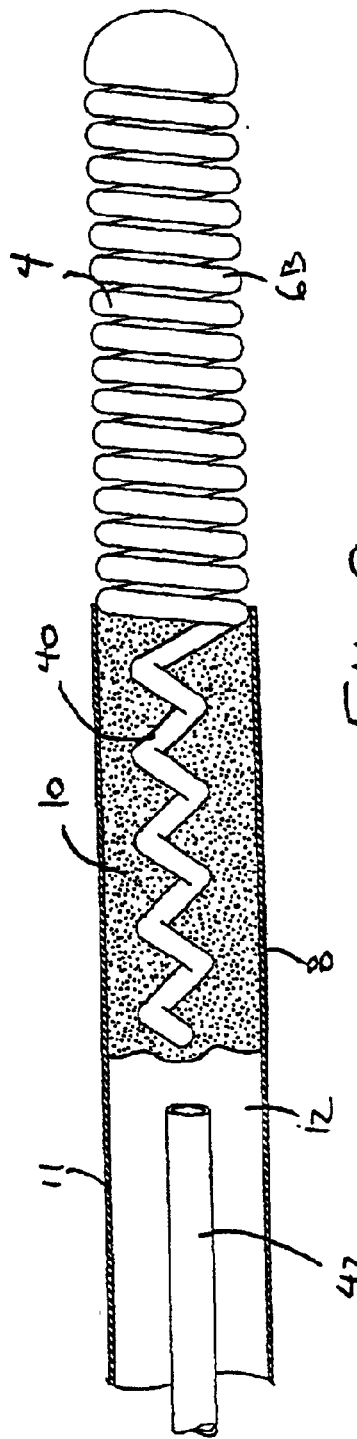
FIG. 9 shows still another device for delivering an occlusion element.
Figure 10:
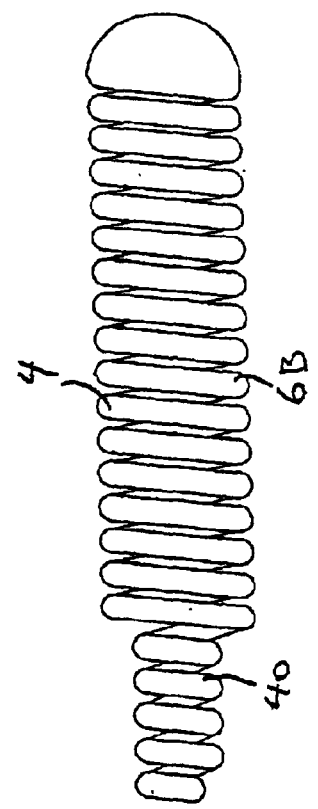
FIG. 10 shows the occlusion element of FIG. 10 released from the delivery element.

Referring to FIGS. 9 and 10, still another device for delivering an occlusion element 6B is shown wherein the same or similar reference numbers refer to the same or similar structure. The occlusion element 6B has a portion 40 embedded in the dissolvable material 10. The portion 40 is preferably naturally biased toward the collapsed position of FIG. 10 when released. The dissolvable material 10 is shown as a solid plug of material 10 but may, of course, have the cavity or throughhole as shown in connection with FIGS. 3–8 without departing from the scope of the invention. A tube 42 delivers, withdraws or otherwise circulates the fluid to dissolve the material 10 at the desired time. The tube 42 and lumen 12 in the delivery element 8 are coupled to the fluid circulating devices 15. The fluid circulating devices 15 may be either the fluid source 16 with pump or a fluid withdrawal device 17, such as a vacuum source or vacuum pump, which are used to circulate the fluid around the material 10. For example, the fluid may be delivered through either the tube 42 or through the annular area between the delivery element 8 and tube 42 with the other element being used to withdraw the fluid. Alternatively, the tube 42 may be used with the fluid withdrawal device 17 to withdraw fluid into the tube 42 while drawing the fluid through the lumen 12. Of course, the fluid may also be simply pulsed one way and then the other so long as the fluid is generally being circulated through the area to dissolve the material 10. One advantage of such as system is that the dissolved material 10 may be withdrawn through the delivery element 8 or tube 42.

The tube 42 and annular area between the delivery element 8 and tube 42 may also be used to prime the device with a suitable fluid. The priming fluid may be a fluid which does not dissolve the material 10 or which dissolves the material 10 very slowly. The tube 42 and annular area between the delivery element 8 and tube 42 may also be used to actively remove air as well as for delivery of the fluid after advancing the device to the desired release site. Although the devices described herein include a separate tube 42, the device 8 may also simply have two lumens instead of the tube 42 without departing from the scope of the invention.

Figure 13:
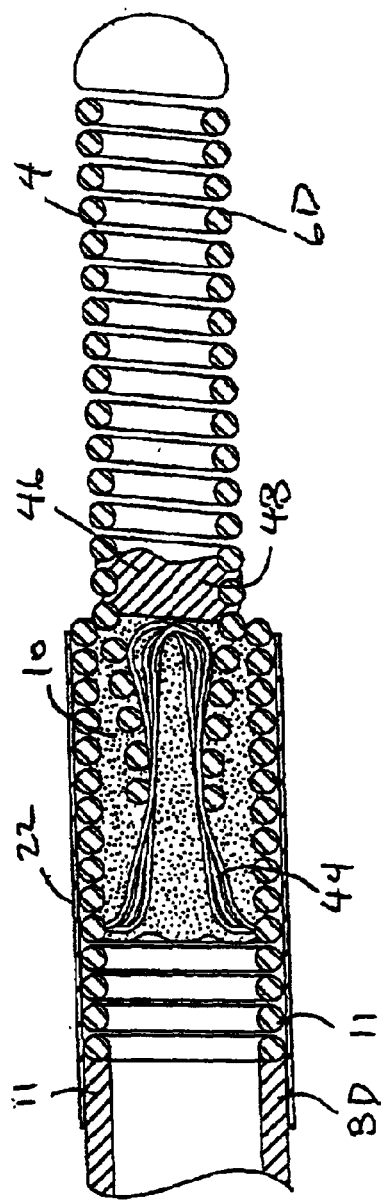
FIG. 13 shows yet another device for delivering an occlusion element.
Figure 14:
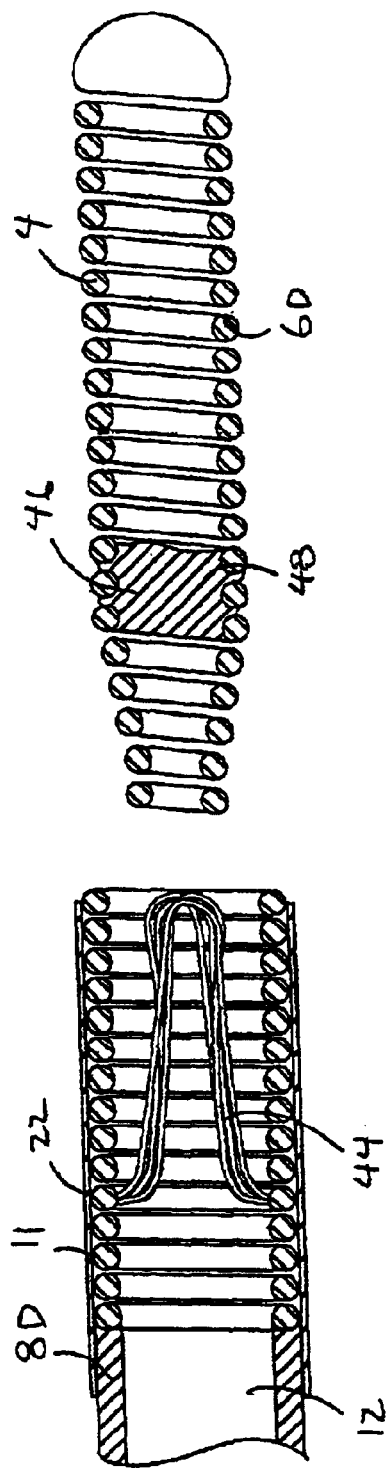
FIG. 14 shows the occlusion element of FIG. 13 released from the delivery element.

Referring to FIGS. 11 and 12, yet another device for delivering an occlusion element 6C is shown wherein the same or similar reference numbers refer to the same or similar structure. The occlusion element 6C has a plurality of filaments 44 embedded in the dissolvable material 10. The tube 42 may be used to circulate the fluid and dissolve the material 10 at the desired time. Referring to FIGS. 13 and 14, still another device 8D for delivering an occlusion element 6D is shown wherein the same or similar reference numbers refer to the same or similar structure. The delivery element 8D has a plurality of filaments 44 embedded in the dissolvable material 10. An advantage of the device 8D is that the filaments 44 are not part of the occlusion element 6D so that the occlusion element 6C may be substantially a conventional occlusion element 6D. The occlusion element 6D also has a distal block 46, which inhibits, and preferably prevents, fluid from entering the distal end of the delivery element 8 to protect the dissolvable material 10 from exposure to blood. The distal block 46 is preferably solder 48 but may be any other suitable material 10.

Referring to FIGS. 15 and 16, yet another device for delivering an occlusion element 6E is shown. The occlusion element 6E has a blocking element 50, which is preferably a first disc 52, which prevents exposure of the material 10 to blood. A second disc 54, or other suitable shape, anchors the occlusion element 6 to the material 10. A third disc 56 serves to move the coil out of the delivery element 8 after melting of the dissolvable material 10. The pressure of the fluid is increased so that the pressure forces on the third disc 56 push the occlusion element 6E out of the delivery element 8. The third disc 56, of course, does not completely prevent proximal exposure of the dissolvable material 10 since the fluid is delivered through the delivery element 8, preferably with the tube, to melt the dissolvable material 10.

Referring to FIGS. 17 and 18, another occlusion element 6F is shown. The occlusion element 6F has a ball 58, preferably 0.005–0.020 in diameter, embedded in the material 10. The ball 58 is attached to the rest of the occlusion element 6F with solder 60 which also serves as a blocking element 63 to prevent distal exposure of the dissolvable material 10. Referring to FIGS. 19 and 20 still another occlusion element 6G is shown which has a cage 62 embedded in the material 10. The cage 62 is attached to the rest of the occlusion element 6 with solder 60 which also serves as the blocking element 63 to prevent distal exposure of the dissolvable material 10.

A method of delivering a medical device, such as an occlusion element 6, is now described in connection with the preferred embodiments, however, it is understood that the method may be practiced with any suitable device. As mentioned above, the invention may be used in any location in the patient's body and use in the cerebral vasculature is described as a particular use of the invention although any other medical device may be delivered to any other part of the body for any other purpose. The guide catheter 5 is introduced into a vessel, such as the femoral artery, and advanced to a suitable location. The microcatheter 12 is then advanced through the guide catheter 5 to a location near the desired site for releasing the occlusion element 6. The invention may be practiced with fewer or more delivery catheters, cannulae or sheaths without departing from the scope of the invention.

The occlusion element 6 is delivered to the desired location by manipulating the delivery element 8. At the desired release time and location, the blocking element (FIG. 2), if used, may be moved to expose at least part of the dissolvable material 10. Fluid is then delivered with the delivery element 8 and/or tube 42 to dissolve the material 10 and release the occlusion element 6. Depending upon the particular embodiment, the release of the occlusion element from the dissolvable bond may completely release the occlusion element 6 from the delivery element 8 or the delivery element 8 may need to be withdrawn to completely release the occlusion element 6. An advantage of requiring additional withdrawal of the delivery element is that the occlusion element 6 may still be manipulated to some degree after release from the dissolvable bond. For example, the delivery element 8 may be advanced and manipulated further to move the occlusion element 6 after dissolution of the material 10.

Figure 21:
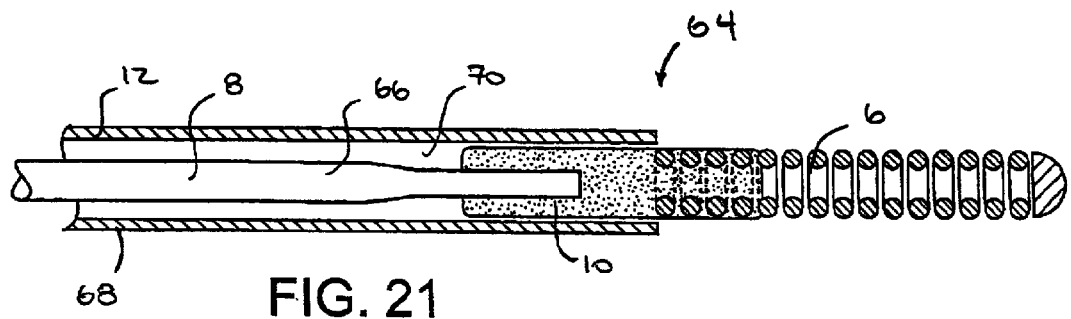
FIG. 21 shows another device for delivering the occluding element.
Figure 22:
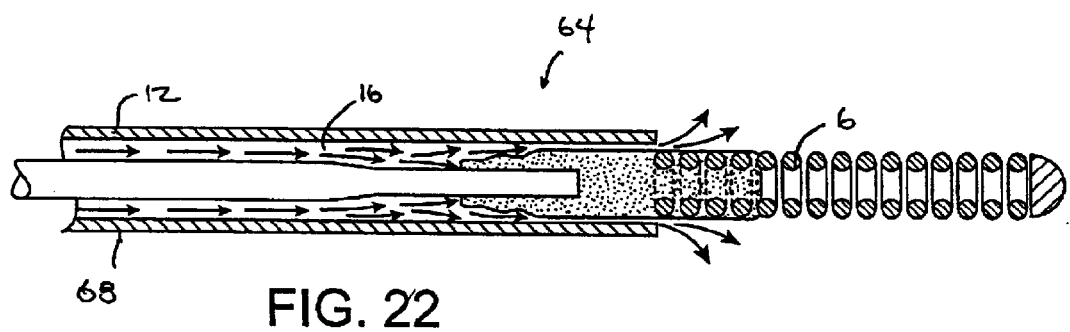
FIG. 22 shows the device of FIG. 21 with the material partially dissolved.
Figure 23:
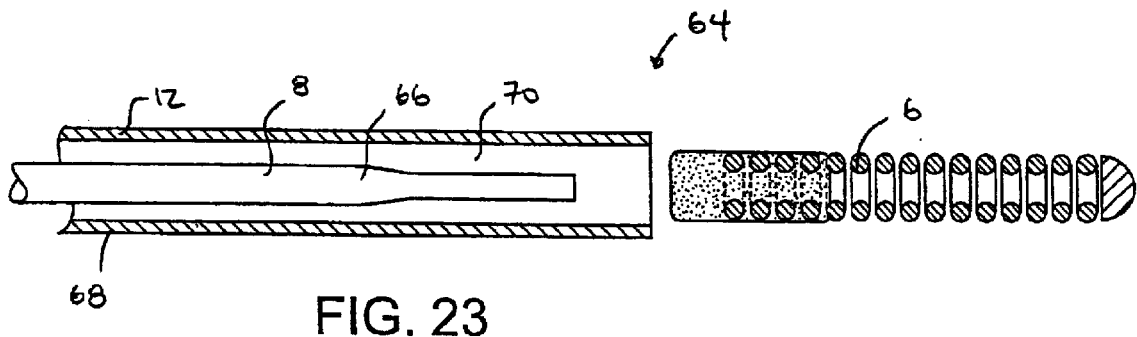
FIG. 23 shows the device of FIGS. 21 and 22 with the material dissolved to release the occlusion element.

Referring to FIGS. 21–23, another device 64 for delivering the occlusion element 6 is shown. The device 64 includes the dissolvable material 10 that dissolves upon application of the fluid 16. As with all of the embodiments described herein, the material 10 and fluid 16 may be any of those described herein or any other suitable combination. The element 6 is mounted to the delivery element 8 which may be a wire 66. The device 64 is advanced through a catheter 68 such as the microcatheter or sheath 12. The device 64 is advanced through a lumen 70 in the catheter 68 and, at the desired time, the fluid 16 is delivered through the lumen 70 to dissolve the material 10. The lumen 70 may be filled or prepped with a fluid which does not dissolve the material 10 during loading and advancement of the element 6 through the catheter 12. For example, the device 64 may be prepped with saline and the fluid used to dissolve the material 10 may utilize a change in pH as described above. FIG. 22 shows the dissolvable material partially dissolved and FIG. 23 shows the element 6 released from the device.

Figure 24:
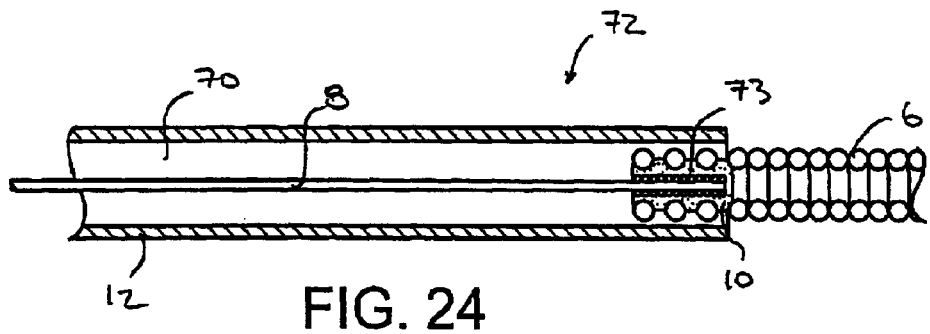
FIG. 24 shows the occluding element mounted over another delivery element with the delivery element having a coil.
Figure 25:
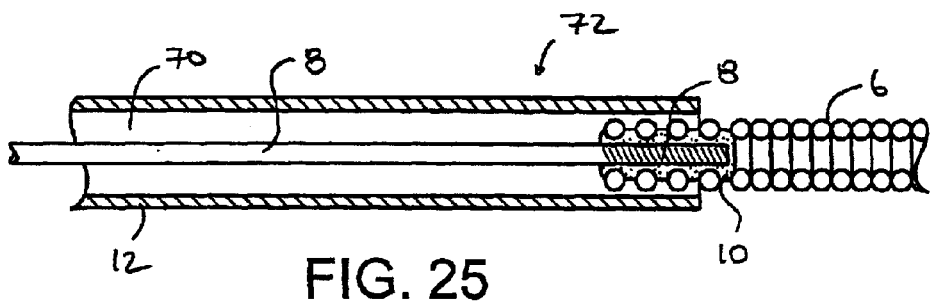
FIG. 25 shows another delivery device having a textured surface over which the dissolvable material is mounted.

Referring to FIGS. 24 and 25, another device 72 for delivering the occlusion element 6 is shown. Similar to the device of FIGS. 21–23, the dissolvable material 10 is dissolved with the fluid delivered through the lumen 70 in the catheter 12. The insertion element 8 may have features which enhance the bond between the insertion element 8 and material 10. For example, a helical wire or ribbon 73 can be wrapped around the insertion element 8 (FIG. 24) or the surface of the insertion element may be roughened or textured (FIG. 25) to enhance engagement with the dissolvable material 10.

Figure 26:
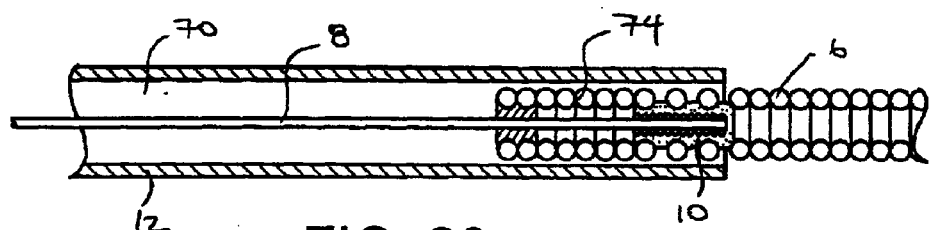
FIG. 26 shows the delivery element having a preloaded portion which exerts a releasing force on the occlusion element.
Figure 27:
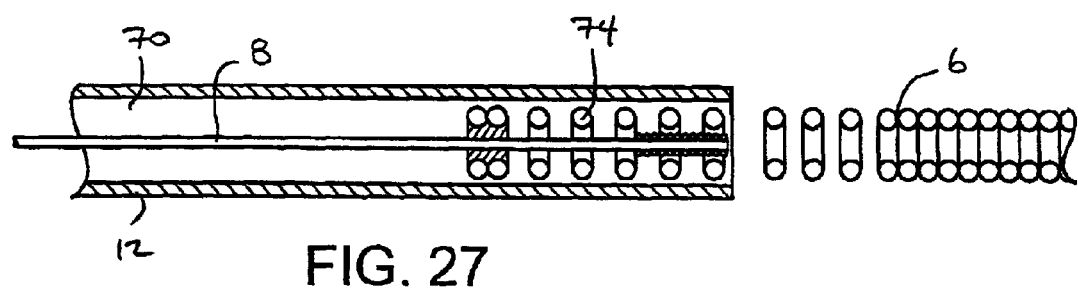
FIG. 27 shows the occlusion element released.

Referring to FIGS. 26 and 27, the devices described herein may also have features which promote detachment of the element 6 from the insertion element 8. For example, the insertion element 8 may exert a force on the occlusion element 6 which helps to detach the occlusion element 6. The pre-loaded force may be imparted in any suitable manner such as with a spring 74. The spring 74 is compressed in the loaded position of FIG. 26. As the material dissolves in the fluid, the spring 74 helps to mechanically disturb the dissolvable material 10 and also tends to force the element 6 away from the insertion element 8. FIG. 27 shows the spring 74 extended after detachment of the occlusion element 6. The spring 74 may be radiopaque so that expansion of the spring may be visualized to monitor release of the device or element.

Figure 28:
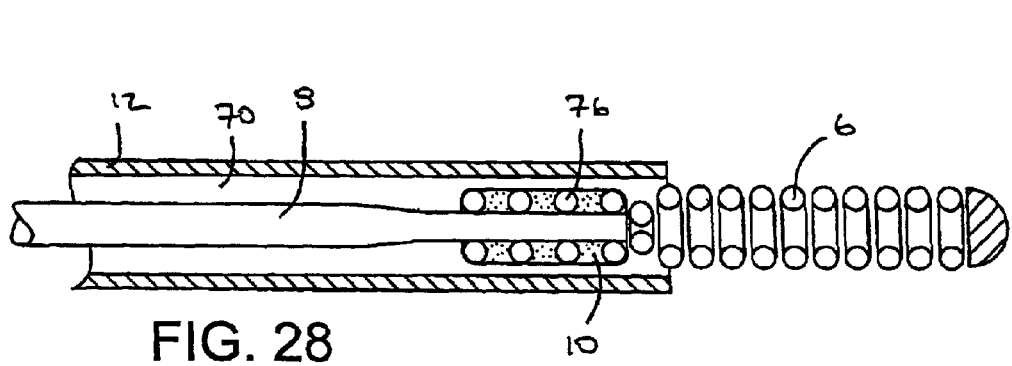
FIG. 28 shows the occlusion element having a preloaded portion embedded in the material.
Figure 29:
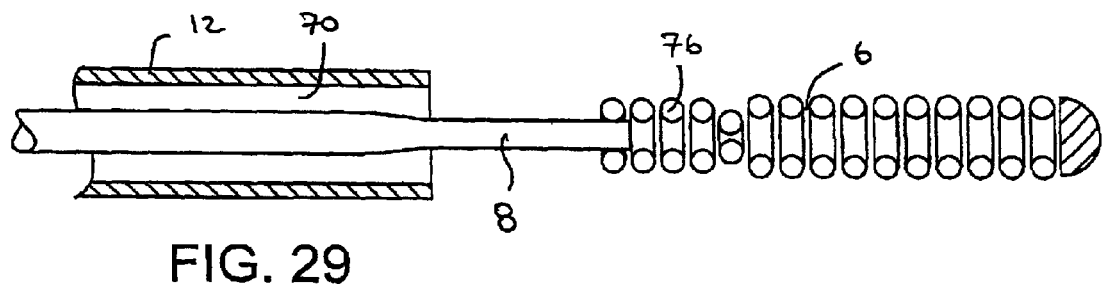
FIG. 29 shows the material dissolved and the occlusion element released.

Referring to FIGS. 28 and 29, the element 6 itself may be pre-loaded to exert forces on the dissolvable material. Proximal windings 76 of the coil 78 can be stretched or compressed to pre-load the windings 76 which are then embedded in the dissolvable material 10. In this manner, the windings 76 themselves act to mechanically disturb the material 10 thereby promoting detachment of the element 6. Pre-loading of the element 6 may be used with any of the embodiments described herein (such as FIG. 9) or other suitable structures.

Figure 30:
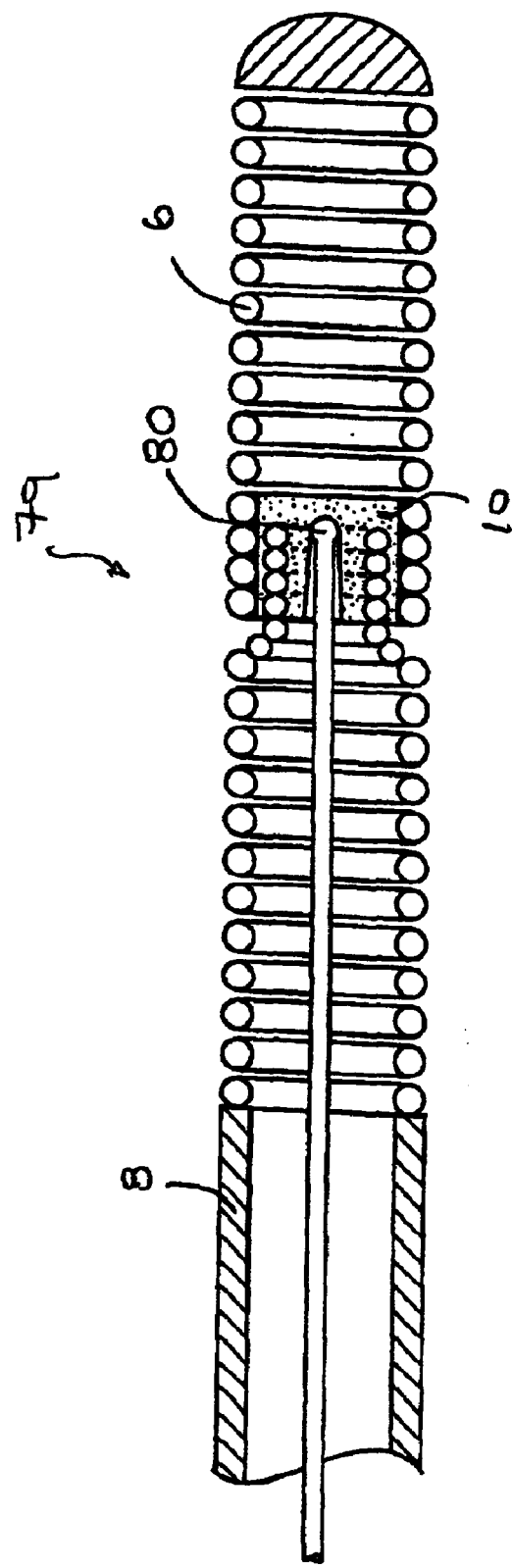
FIG. 30 shows a heating element which is used to heat the material to aid in dissolution of the material.

Referring to FIG. 30, another device 79 for delivering the medical device, such as the occlusion element 6, is shown. The device 79 also has the fluid dissolvable material 10 that is dissolved to release the element 6. Similar to the use of a pH change to enhance dissolution, the material 10 may dissolve at a faster rate at a selected temperature. The temperature may be changed by simply heating or cooling the fluid or by heating the material 10 itself. The fluid may be heated and cooled with the fluid circulating device 15 or with an element mounted to the device itself. For example, a heating element 80, which may use simple resistive heating, may be mounted to the device or delivered through a lumen in the device to heat the material 10. Referring to FIG. 30, the heating element directly contacts the material 10 to heat the material 10.

Figure 31:
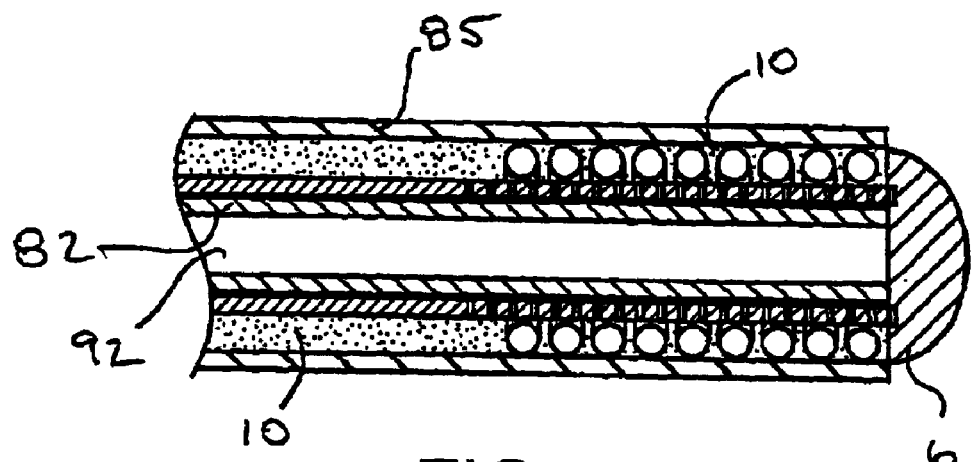
FIG. 31 shows another system for delivering the occlusion element.
Figure 32:
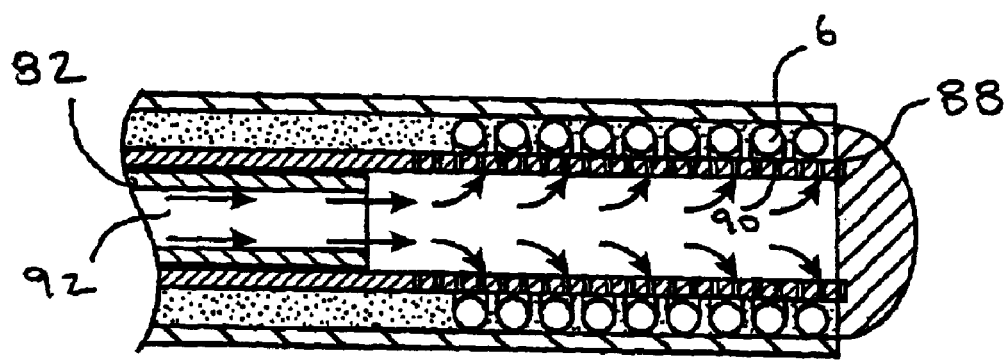
FIG. 32 shows the system of FIG. 31 with a tube retracted to expose the material.

Referring to FIGS. 31 and 32, another blocking element 82 is shown which protects the dissolvable material 10. The blocking element 82 is a tube 84 that covers an interior surface 86 of the material 10. An outer tube 85 covers the outer surface of the material 10. The blocking element 82 is retracted to expose an inner tube 88 having openings 90 therein which permit fluid to contact the material 10 as shown in FIG. 32. The inner tube 88 may also be retracted to further expose the dissolvable material or the inner tube 88 may be omitted altogether. The fluid is delivered through a lumen 92 to dissolve the material 10.

Figure 33:
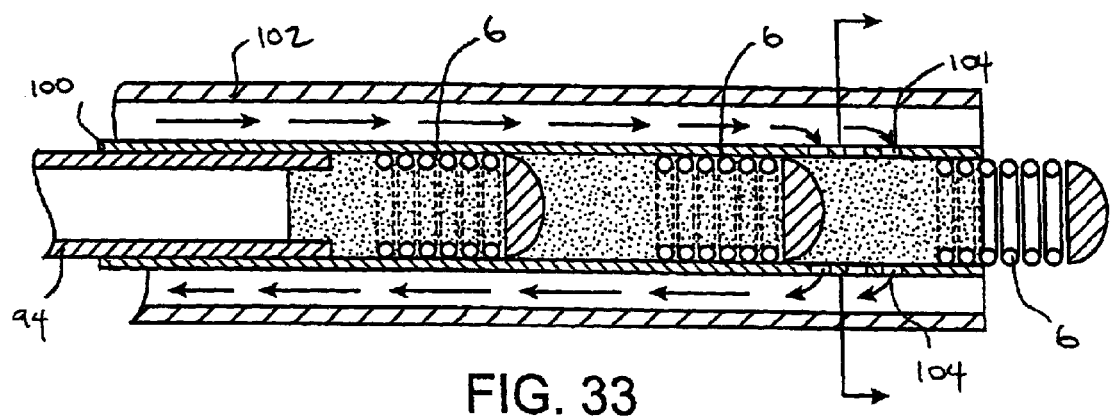
FIG. 33 shows a system for delivering a number of occlusion elements.
Figure 34:
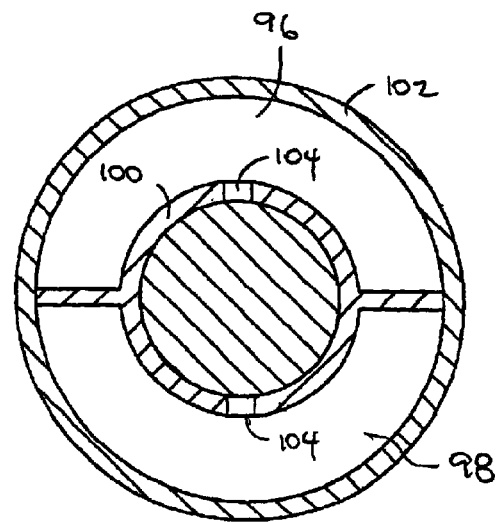
FIG. 34 is a cross-sectional view of the system of FIG. 33 along line I—I.

The present invention may also be used to deliver a number of elements 6 with the same delivery element 94. Referring to FIGS. 33 and 34, a number of the elements 6 are mounted to the insertion element 94 which may be a tube, shaft, wire or mandrel. The elements 6 are coupled to one another with the dissolvable material 10 to form a dissolvable connection between each of the elements. Two lumens 96, 98 are formed between inner and outer tubes 100, 102 with the fluid being delivered through one of the lumens 96 and withdrawn through the other lumen 98 (FIG. 34). The fluid passes through openings 104 in the inner tube 100 and into contact with the dissolvable material 10. The fluid, together with the dissolved material 10, is then withdrawn through openings 106 in the other side of the inner tube 100 and out through the other lumen 98. After the occlusion element 6 has been released, the delivery element 94 is advanced to position another of the dissolvable connections between the openings 104, 106 to dissolve another connection. This process is repeated until all of the occlusion elements 6, or a desired number, have been released.

Figure 35:
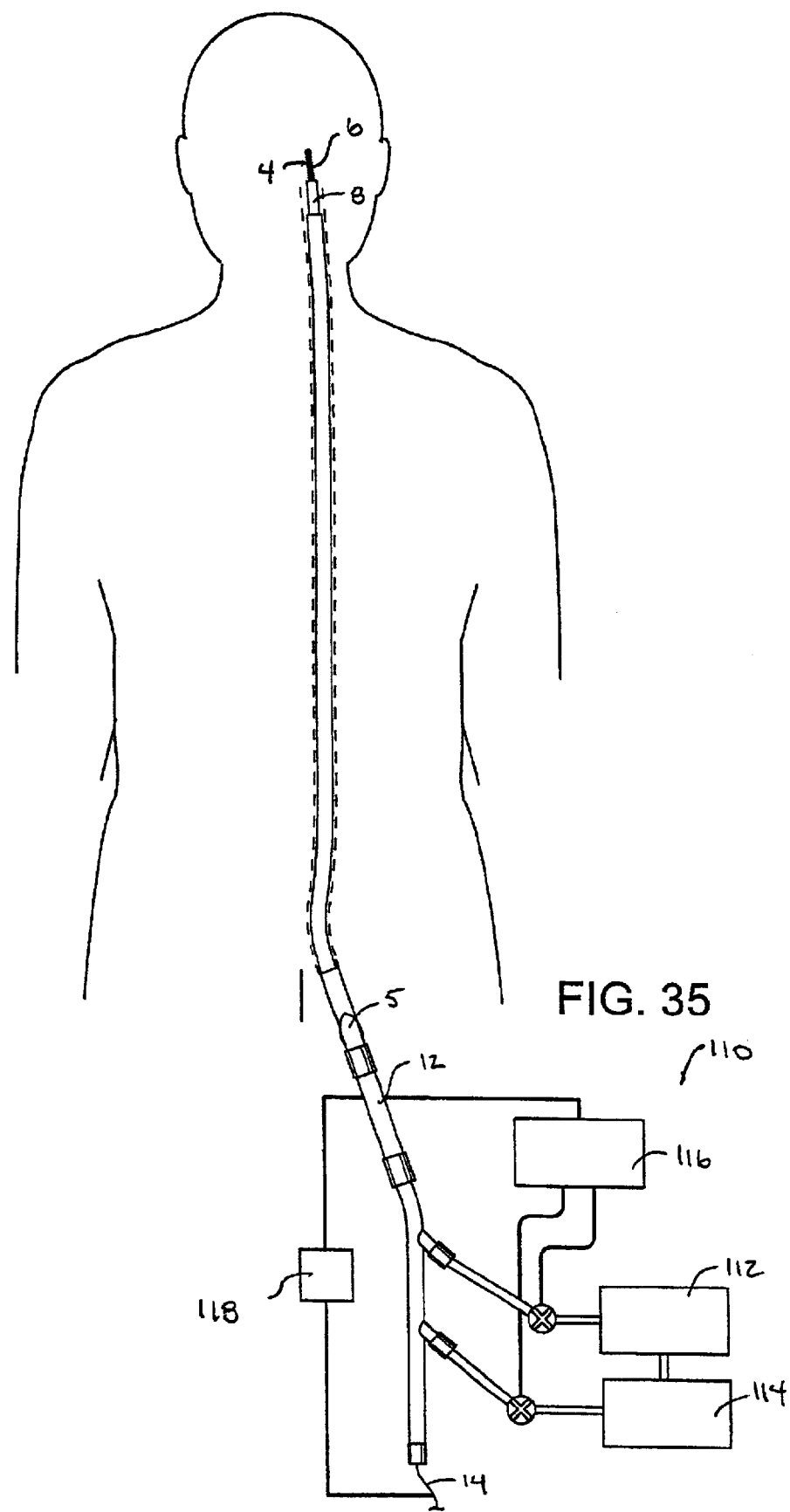
FIG. 35 shows another system for use with the devices and methods of the present invention.

Referring to FIG. 35, a system 110 for flushing the device with a flushing fluid 112 is shown. The flushing fluid 112 is delivered to eliminate the fluid 114 used to dissolve the material 10. Flushing the system is particularly useful when delivering a number of elements 6 with the same delivery device to prevent premature release or degradation of the dissolvable connections. The flushing fluid 112 and fluid 114 used to dissolve the material may be coupled to a fluid control system 116 that controls delivery of the two fluids. The fluid control system 116 may include a detector 118, described below, which detects when an element 6 has been released so that the flushing fluid 112 can then be delivered. When the user desires to deliver another element 6, the user prompts the system to switch back to delivery of the fluid 114 which dissolves the material for release of another element 6.

As mentioned above, the detector 118 is particularly useful with the multiple element system described above but may be used to simply alert the user when the element 6 has been detached so that the user manipulates the insertion element appropriately once detachment has occurred. Detecting detachment of the element 6 may also be used to determine when to flush the system with the flushing fluid 112. One method of detecting detachment is to apply energy to the device and detect a change in a measured parameter or characteristic of the energy. For example, the detector 118 may apply a low power RF signal with the standing wave ratio (SWR) being measured. The SWR will change when the element 6 has been released so long as an appropriate frequency and/or wavelength is selected. Other types of energy, such as electrical energy, may be used while measuring other parameters, such as electrical resistance, without departing from the scope of the invention.

Figure 36:
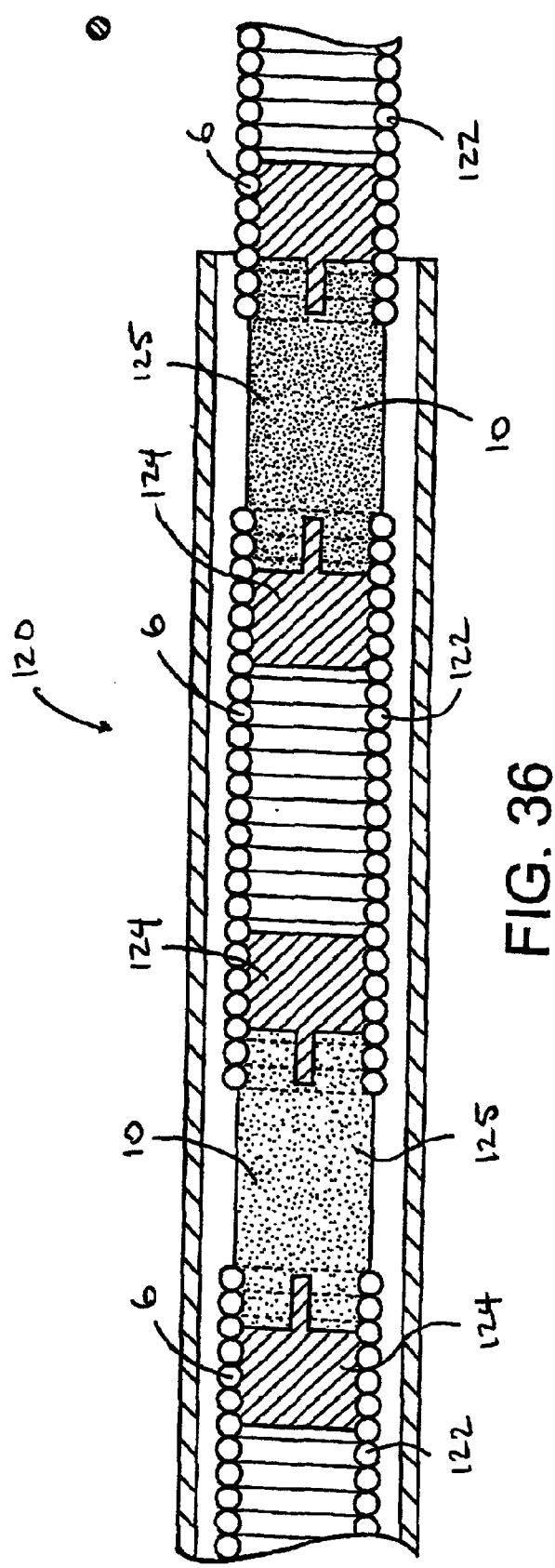
FIG. 36 shows another multiple element delivery system.

Referring to FIG. 36, another multiple release system 120 is shown. The occlusion elements 6 have coils 122 with a hub 124 mounted to each end. The coils 122 and hub 124 are embedded in the dissolvable material 10 to form a dissolvable connection 125 between each of the elements 6. In another aspect of the invention, different fluids may be used to dissolve each of the connections 125 between the occlusion elements 6. In this manner, premature release of one or more of the elements 6 or premature degradation of the material 10 is reduced. For example, the pH may be varied to preferentially dissolve the connections 125 one at a time with each of the connections being dissolved by a different pH fluid.

Referring to FIGS. 37 and 38, another system 127 for releasing the occlusion element 6 is shown. The occlusion element 6 has a portion 128 embedded in the dissolvable material. The portion 128 preferably includes a flexible filament 130, such as suture, which is attached to the element 6. The filament 130 may be one or more filaments 130 extending somewhat independently similar to FIGS. 11–14 or may form a wound, woven or braided structure. The fluid is delivered through a lumen 129 to dissolve the material and release the occlusion element 6 as shown in FIG. 38.

Referring to FIGS. 39 and 40, still another system 131 for releasing the occlusion element 6 is shown. The occlusion element has an embedded portion 134 which is embedded in the dissolvable material. The embedded portion 134 is also preloaded under tension but could also be preloaded under compression. The portion may be any suitable structure such as a first coil 136 attached to a second coil 138. The first coil 136 is relatively flexible and stretches to the expanded position of FIG. 39 while the second coil 138 is stiffer and expands less. When released, the embedded or preloaded portion 134 moves to the position shown in FIG. 40. The embedded portion 134 moves into the occlusion element 6, and specifically within the coils, so that the embedded portion does not protrude from the coil a significant distance when deployed.

Referring to FIGS. 41 and 42, another system 135 for releasing an occlusion element 6 is shown. The system has a delivery element 140 having an extension 142 which extends into the occlusion element 6 and, in particular, inside a cavity 144 such as the windings of the occlusion element 6. In this manner, the delivery element 140 protects the dissolvable material and acts like a blocking element in the manner described herein. The extension 142 also helps to reinforce the area around the dissolvable material 10 to prevent mechanical disturbance of the dissolvable material 110 when the catheter is bent or twisted during advancement. A tube or stylet 144 may be positioned in the delivery element to improve column strength during delivery. Fluid is delivered through the lumen 146 to dissolve the material at the desired time. The fluid flows out of the extension 142 and into contact with dissolvable material 10. The delivery element, like any of the delivery elements or catheters described herein, may have increased flexibility toward the distal end as is known in the art.

The present invention has been described in connection with the preferred embodiments, however, many variations and alternative embodiments fall within the scope of the invention. For example, the occlusion element may have any shape and may be made of any material. Furthermore, although it is preferred to deliver the fluid to the dissolvable material, the material may also be dissolved by simply coming into contact with the patient's blood without departing from various aspects of the invention. The dissolvable material may completely detach the occlusion element from the delivery element or may require another action, such as withdrawal of the delivery element, to fully release the occlusion element. Finally, the methods and devices of the present invention may be used with any medical device and not necessarily the occlusion elements described herein and use with any suitable medical device falls within the scope of the invention so that the term medical device or element may be substituted for occlusion element or device as used herein. Thus, the description of the preferred embodiments should not limit the invention. The invention has been described in connection with a number of different features, aspects and advantages which should be considered independently and, thus, no single aspect or advantage of the invention should be considered an essential element of the invention. For example, various aspects of the invention may be practiced with or without various aspects such as the blocking element, sheath, or fluid circulation.

What is claimed is:

1. A method of delivering an occlusion element, comprising the steps of:
   providing an occlusion element which is coupled to a delivery element with a dissolvable material, the dissolvable material being dissolvable with a fluid, the dissolvable material forming a dissolvable connection between the delivery element and the occlusion element;
   advancing the occlusion element through a patient's vascular system with the occlusion element coupled to the delivery element with at least the dissolvable connection; and
   dissolving the dissolvable material thereby releasing the occlusion element from the dissolvable connection with the delivery element, wherein the dissolving step is carried out with the dissolvable material being dissolved faster by the fluid as compared to other fluids contacting the material during the advancing step.

2. The method of claim 1, wherein:
   the providing step is carried out with the dissolvable material dissolving faster at a selected pH as compared to a pH of other fluids which the material contacts during the advancing step; and
   the dissolving step is carried out by delivering a fluid having the selected pH to dissolve the dissolvable material.

3. The method of claim 1, wherein:
   the dissolving step is carried out with the dissolvable material and fluid being a solute and solvent.

4. The method of claim 1, wherein:
   the dissolving step is carried out by delivering a fluid to the dissolvable material, the fluid being an acid.

5. The method of claim 4, wherein the dissolvable material includes a material selected from the group consisting of zinc and iron.

6. The method of claim 1, wherein:
   the dissolving step is carried out by delivering a fluid to the dissolvable material, the fluid being a base.

7. The method of claim 1, wherein:
   the dissolving step is carried out by delivering the fluid to the material to dissolve the dissolvable material.

8. The method of claim 7, wherein:
   the dissolving step is carried out with the fluid being delivered through the delivery element.

9. The method of claim 8, wherein:
   the dissolving step is carried out with a tube positioned in the delivery element, the tube having a lumen, the tube and delivery element defining a space therebetween, the fluid being delivered through one of the lumen and the space and the fluid being withdrawn through the other of the lumen and the space.

10. The method of claim 1, wherein:
    the providing step is carried out with the occlusion element forming coils.

11. The method of claim 1, wherein:
    the providing step is carried out with the dissolvable material having a cavity.

12. The method of claim 11, wherein:
    the providing step is carried out with the cavity being a throughhole.

13. The method of claim 1, further comprising the step of:
    positioning a blocking element to impede fluid contact with a least a protected portion of the dissolvable material, the blocking element being movable to a position spaced apart from the protected portion of the dissolvable material.

14. The method of claim 13, wherein:
    the blocking element is positioned in a cavity in the dissolvable material.

15. The method of claim 14, wherein:
    the providing step is carried out with the blocking element being a tube; and the method further comprising the step of retracting the tube to expose at least part of the dissolvable material.

16. The method of claim 14, wherein:
    the providing step is carried out with the blocking element being a tube; and
    the dissolving step being carried out with the fluid passing through the tube.

17. The method of claim 1, wherein:
    the providing step is carried out with the occlusion element having a portion embedded in the dissolvable material.

18. The method of claim 17, wherein:
    the providing step is carried out with the embedded portion being embedded in the dissolvable material in an expanded position, the embedded portion being naturally biased toward a collapsed position; and
    the dissolving step is carried out so that the portion of the occlusion element is no longer embedded in the material thereby permitting the portion to move toward the collapsed position.

19. The method of claim 17, wherein:
    the providing step is carried out with the portion embedded in the material including a plurality of filaments.

20. The method of claim 17, wherein:
    the providing step is carried out with the portion embedded in the dissolvable material being a coil.

21. The method of claim 1, wherein:
the providing step is carried out with the occlusion element having a plurality of flexible fibers embedded in the dissolvable material.

22. The method of claim 1, wherein:
the providing step is carried out with the portion embedded in the material including a ball.

23. The method of claim 1, wherein:
the providing step is carried out with the portion embedded in the material including a cage.

24. The method of claim 1, wherein:
the providing step is carried out with a flexible sheath covering at least a portion of the dissolvable material.

25. The method of claim 24, wherein:
the providing step is carried out with the sheath having openings therein.

26. The method of claim 25, wherein:
the providing step is carried out with the delivery element having a fluid distributing portion with openings for distributing the fluid;
the dissolving step being carried out to deliver the fluid through the openings in the distributing portion to dissolve the material.

27. The method of claim 26, wherein:
the providing step is carried out with the distributing portion being conical.

28. The method of claim 1, further comprising the step of:
moving the delivery element relative to the occlusion element after the dissolving step to fully release the occlusion element from the delivery element.

29. The method of claim 1, wherein:
the dissolving step fully releases the occlusion element from the delivery element.

30. The method of claim 1, wherein:
the providing step is carried out with the occlusion element having a blocking portion which isolates the material from the patient's blood;
the advancing step being carried out so that the blocking portion isolates the material from the patient's blood during the advancing step.

31. The method of claim 30, wherein:
the providing step is carried out with the blocking portion being a plug of material.

32. The method of claim 31, wherein:
the providing step is carried out with the plug of material being solder.

33. The method of claim 30, wherein:
the providing step is carried out with the blocking portion being a disc.

34. The method of claim 1, wherein:
the dissolving step is carried out with the fluid being a fluid selected from the group consisting of water, saline and the patient's own blood.

35. The method of claim 1, wherein:
the providing step is carried out with the material being selected from the group consisting of sugar, salt, mannitol or a combination thereof.

36. The method of claim 35, wherein:
the dissolving step is carried out by using a first fluid to dissolve one of the dissolvable connections and a second fluid, different than the first fluid, to dissolve another of the dissolvable connections.

37. A method of delivering an occlusion element, comprising the steps of:
providing an occlusion element which is coupled to a delivery element with a dissolvable material, the dissolvable material being dissolvable with a fluid, the dissolvable material forming a dissolvable connection between the delivery element and the occlusion element;
advancing the occlusion element through a patient's vascular system with the occlusion element coupled to the delivery element with at least the dissolvable connection; and
dissolving the dissolvable material thereby releasing the occlusion element from the dissolvable connection with the delivery element, wherein the dissolvable material is a polymer.

38. The method of claim 37, wherein the dissolvable material is a natural polymer.

39. The method of claim 37, wherein the dissolvable material is an alginate.

40. The method of claim 37, wherein the dissolvable material is a cross-linked polymer.

41. The method of claim 40, wherein the dissolving step is carried out by delivering a fluid including a cation which dissolves the cross-linked polymer.

42. The method of claim 37, wherein the polymer is in the form of polymer layers bonded together.

43. The method of claim 42, wherein the polymer is an acrylic polymer.

44. The method of claim 42, wherein the polymer is a methacrylate polymer.

45. The method of claim 42, wherein the dissolving step is carried out by delivering a fluid having a pH different than blood.

46. The method of claim 42, wherein the dissolving step is carried out by using a fluid having a salinity different than blood.

47. The method of claim 46, wherein the dissolving step is carried out with the fluid having a pH of 4–6.5.

48. The method of claim 46, wherein the dissolving step is carried out with the fluid having a pH of 8–95.

49. The method of claim 46, wherein the dissolving step is carried out with the fluid having a pH of less than 7.0.

50. The method of claim 46, wherein the dissolving step is carried out with the fluid having a pH of greater than 7.4.

51. A method of delivering an occlusion element, comprising the steps of:
providing an occlusion element which is coupled to a delivery element with a dissolvable material, the dissolvable material being dissolvable with a fluid, the dissolvable material forming a dissolvable connection between the delivery element and the occlusion element;
advancing the occlusion element through a patient's vascular system with the occlusion element coupled to the delivery element with at least the dissolvable connection; and
dissolving the dissolvable material thereby releasing the occlusion element from the dissolving connection with the delivery element; and
changing a temperature of the dissolvable material during the dissolving step.

52. The method of claim 51, wherein:
the temperature changing step is carried out by delivering the fluid at a temperature which changes the temperature of the dissolvable material.

53. The method of claim 51, wherein:
the temperature changing step is carried out by directly heating the dissolvable bond.

54. The method of claim 53, wherein:

the temperature changing step is carried out by using resistive heating.

55. A method of delivering an occlusion element, comprising the steps of:

providing an occlusion element which is coupled to a delivery element with a dissolvable material, the dissolvable material being dissolvable with a fluid, the dissolvable material forming a dissolvable connection between the delivery element and the occlusion element, the providing step being carried out with a flexible sheath extending over the dissolvable material, the flexible sheath being attached to the delivery element;

advancing the occlusion element through a patient's vascular system with the occlusion element coupled to the delivery element with at least the dissolvable connection; and dissolving the dissolvable material thereby releasing the occlusion element from the dissolvable connection with the delivery element.

56. A method of delivering an occlusion element, comprising the steps of:

providing an occlusion element which is coupled to a delivery element with a dissolvable material, the dissolvable material being dissolvable with a fluid, the dissolvable material forming a dissolvable connection between the delivery element and the occlusion element, the providing step being carried out with the delivery element having a plurality of occlusion elements;

advancing the occlusion element through a patient's vascular system with the occlusion element coupled to the delivery element with at least the dissolvable connection; and dissolving the dissolvable material thereby releasing the occlusion element from the dissolve connection with the delivery element, the dissolving step being carried out a number of times to sequentially release the plurality of occlusion elements.

57. The method of claim 56, wherein:

the providing step is carried out with the delivery element including a tube in which the plurality of occlusion elements is positioned;

the dissolving step being carried out by moving the tube relative to the occlusion elements to expose the dissolvable material to the fluid.

58. The method of claim 55, wherein;

the providing step is carried out with the tube having openings therein through which the fluid passes to contact the dissolvable material.

59. The method of claim 58, wherein:

the providing step is carried out with the delivery element having an outer tube positioned around the tube; and the dissolving step is carried out by delivering the fluid through a lumen positioned between the tube and outer tube.

60. The method of claim 59, wherein:

the dissolving step is carried out by withdrawing the fluid and dissolved parts of the dissolvable material through another lumen between the tube and outer tube.

61. A method of delivering a occlusion element, comprising the steps of:

providing an occlusion element which is coupled to a delivery element with a dissolvable material, the dissolvable material being dissolvable with a fluid, the dissolvable material forming a dissolvable connection between the delivery element and the occlusion element;

advancing the occlusion element through a patient's vascular system with the occlusion element coupled to the delivery element with at least the dissolvable connection; and dissolving the dissolvable material thereby releasing the occlusion element from the dissolvable connection with the delivery element; and detecting whether the occlusion element has been released from the delivery element.

62. The method of claim 61, wherein:

the detecting step is carried out by applying energy to the delivery element and detecting a change in a parameter thereby indicating release of the occlusion element.

63. The method of claim 62, wherein:

the detecting step is carried out by applying RF energy.

64. The method of claim 63, wherein:

the detecting step is carried out with the parameter being the standing wave ratio.

65. A method of delivering a medical device, comprising the steps of:

providing a medical device which is coupled to a delivery element with a dissolvable material, the dissolvable material being dissolvable with a fluid, the dissolvable material forming a dissolvable bond between the delivery element and the medical device;

advancing the medical device into a patient with the medical device coupled to the delivery element; and dissolving the dissolvable material thereby releasing the medical device from the delivery element.

* * * * *